United States Patent
Dickinson et al.

(10) Patent No.: US 11,116,937 B2
(45) Date of Patent: Sep. 14, 2021

(54) FOLEY CATHETER AND CORRESPONDING SINGLE-LAYER TRAY PACKAGING SYSTEM

(71) Applicant: Medline Industries, Inc, Northfield, IL (US)

(72) Inventors: Sarah Dickinson, Glen Ellyn, IL (US); Saul Godinez, Chicago, IL (US); Lindsay Hilbelink, Salem, WI (US)

(73) Assignee: Medline Industries, Inc., Northfield, IL (US)

( * ) Notice: Subject to any disclaimer, the term of this patent is extended or adjusted under 35 U.S.C. 154(b) by 228 days.

(21) Appl. No.: 15/977,944

(22) Filed: May 11, 2018

(65) Prior Publication Data

US 2019/0344044 A1    Nov. 14, 2019

(51) Int. Cl.
*A61M 25/00* (2006.01)
*B65D 85/00* (2006.01)

(52) U.S. Cl.
CPC ........... *A61M 25/002* (2013.01); *B65D 85/00* (2013.01)

(58) Field of Classification Search
CPC .................. A61M 25/002; A61M 25/0017
See application file for complete search history.

(56) References Cited

U.S. PATENT DOCUMENTS

| | | | |
|---|---|---|---|
| 2,659,485 A | 11/1953 | Duley et al. | |
| 2,715,296 A | 8/1955 | Petit | |
| 2,781,611 A | 2/1957 | West | |
| 2,886,316 A | 5/1959 | Ayala | |
| 2,947,415 A | 8/1960 | Garth | |
| 2,954,642 A | 10/1960 | Roderick | |
| 2,959,891 A | 11/1960 | Barnett et al. | |
| 3,013,656 A | 12/1961 | Murphy, Jr. | |
| 3,107,786 A | 10/1963 | Adelman | |
| 3,133,635 A | 5/1964 | Morris | |
| 3,166,189 A | 1/1965 | Disston | |

(Continued)

FOREIGN PATENT DOCUMENTS

| | | |
|---|---|---|
| CA | 6012586 | 1/2000 |
| CN | 201823147 | 5/2011 |

(Continued)

OTHER PUBLICATIONS

[*Medline Industries Inc* vs *C.R Bard. Inc.*, Exhibit G to Declaration of Dylan J. Raife in Support of Bard Opening Claim Construction Brief; Civil Action No. 1:16-cv-03529; Judge Sharon Johnson Coleman; Filed Nov. 11, 2016.

(Continued)

*Primary Examiner* — Tatyana Zalukaeva
*Assistant Examiner* — Jessica R Arble
(74) *Attorney, Agent, or Firm* — Philip H. Burrus, IV

(57) ABSTRACT

A medical procedure kit includes a single-layer tray (100) having a first compartment (101) at least partially bounded by a first base member (107) and a second compartment (102) at least partially bounded by a second base member (108). At least one syringe (901) is situated within the first compartment. A Foley catheter (701), coupled to coiled tubing (702) and a fluid drain bag (703), is disposed within the second compartment. This catheter assembly is inverted, with the Foley catheter (701) and the coiled tubing (702) positioned between the second base member (108) and the fluid drain bag (703).

20 Claims, 11 Drawing Sheets

(56) References Cited

U.S. PATENT DOCUMENTS

| | | |
|---|---|---|
| 3,315,802 A | 4/1967 | Maro |
| 3,329,261 A | 7/1967 | Serany, Jr. et al. |
| D209,641 S | 12/1967 | Goldberg |
| 3,379,339 A | 4/1968 | Asenbauer |
| 3,485,352 A | 12/1969 | Pilger |
| D218,077 S | 7/1970 | Gabriel |
| 3,542,019 A | 11/1970 | Gittins |
| 3,726,281 A | 4/1973 | Norton |
| 3,770,119 A | 11/1973 | Hultberg et al. |
| 3,851,649 A | 12/1974 | Villari |
| D234,404 S | 2/1975 | Merril |
| 3,901,235 A | 8/1975 | Patel et al. |
| D237,315 S | 10/1975 | Nowakowski |
| D237,317 S | 10/1975 | Norkowski |
| 3,965,900 A | 6/1976 | Boedecker |
| 3,967,728 A | 7/1976 | Gordon et al. |
| 3,976,195 A | 8/1976 | Cohen |
| 3,978,983 A | 9/1976 | Brezetta |
| D242,654 S | 12/1976 | Rawls |
| 3,998,221 A | 12/1976 | Collins |
| D243,798 S | 3/1977 | Swartz |
| 4,011,944 A | 3/1977 | Cooley |
| 4,053,280 A | 10/1977 | Salisbury |
| 4,075,782 A | 2/1978 | Neuschatz |
| D248,871 S | 8/1978 | Forsman et al. |
| D249,362 S | 9/1978 | Forsman et al. |
| 4,140,127 A | 2/1979 | Cianci et al. |
| 4,160,505 A | 7/1979 | Rauschenberger |
| 4,170,300 A | 10/1979 | Pick |
| 4,226,328 A | 10/1980 | Beddow |
| 4,266,669 A | 5/1981 | Watson |
| 4,269,310 A | 5/1981 | Uson |
| 4,282,678 A | 8/1981 | Tsui |
| 4,307,539 A | 12/1981 | Klein |
| D262,995 S | 2/1982 | Gaba et al. |
| 4,334,537 A | 6/1982 | Peterson |
| D268,130 S | 3/1983 | Easton |
| 4,458,705 A | 7/1984 | Cawood |
| D275,886 S | 10/1984 | Sheward et al. |
| D276,462 S | 11/1984 | Villarreal |
| D277,508 S | 2/1985 | Clair |
| 4,501,363 A | 2/1985 | Isbey, Jr. |
| 4,523,679 A | 6/1985 | Paikoff et al. |
| 4,530,349 A | 7/1985 | Metzger |
| D280,663 S | 9/1985 | Albon et al. |
| D280,933 S | 10/1985 | McLaughlin |
| D280,993 S | 10/1985 | Mariol |
| D283,051 S | 3/1986 | Fichera |
| D287,760 S | 1/1987 | Discko, Jr. |
| 4,761,008 A | 8/1988 | Huggins |
| 4,767,008 A | 8/1988 | Warnecke et al. |
| 4,795,441 A | 1/1989 | Bhatt |
| 4,811,847 A | 3/1989 | Reif |
| 4,828,113 A | 5/1989 | Friedland |
| 4,844,259 A | 7/1989 | Glowczewskie et al. |
| 4,858,821 A | 8/1989 | Bickelhaupt |
| 4,925,448 A | 5/1990 | Bazaral |
| 4,928,830 A | 5/1990 | Brewer |
| D310,896 S | 9/1990 | Winjum |
| 4,991,877 A | 2/1991 | Lieberman |
| 5,007,535 A | 4/1991 | Meseke et al. |
| 5,024,326 A | 6/1991 | Sandel et al. |
| 5,031,768 A | 7/1991 | Fischer |
| 5,094,621 A | 3/1992 | Friedel |
| 5,163,557 A | 11/1992 | Sokolowski |
| 5,170,804 A | 12/1992 | Glassman |
| 5,197,885 A | 3/1993 | Friedel |
| D334,973 S | 4/1993 | Valentine et al. |
| D337,830 S | 7/1993 | Coyne et al. |
| 5,232,369 A | 8/1993 | Mavrikis |
| 5,242,398 A | 9/1993 | Knoll et al. |
| 5,244,394 A | 9/1993 | Serabian-Musto |
| D343,687 S | 1/1994 | Houghton et al. |
| 5,289,919 A | 3/1994 | Fischer |
| 5,312,287 A | 5/1994 | Chuang |
| 5,314,339 A | 5/1994 | Aponte |
| 5,318,543 A | 6/1994 | Ross et al. |
| 5,324,201 A | 6/1994 | Friedel |
| 5,339,955 A | 8/1994 | Horan et al. |
| D351,661 S | 10/1994 | Fischer |
| 5,392,918 A | 2/1995 | Harrison |
| 5,411,437 A | 5/1995 | Weber et al. |
| 5,487,566 A | 1/1996 | Hedge, Jr. |
| D380,272 S | 6/1997 | Partika et al. |
| 5,665,945 A | 9/1997 | Oshima |
| D387,177 S | 12/1997 | Davis |
| D387,559 S | 12/1997 | Williamson |
| 5,713,778 A | 2/1998 | Radosevich et al. |
| 5,720,502 A | 2/1998 | Cain |
| 5,778,574 A | 7/1998 | Reuben |
| 5,779,053 A | 7/1998 | Partika |
| 5,795,213 A | 8/1998 | Goodwin |
| 5,810,738 A | 9/1998 | Thomas, II |
| 5,820,441 A | 10/1998 | Pracas |
| 5,827,262 A | 10/1998 | Neftel et al. |
| 5,829,790 A | 11/1998 | Phillips |
| 5,872,262 A | 2/1999 | Dolle, III et al. |
| 5,931,303 A | 8/1999 | Salvadori |
| 5,941,241 A | 8/1999 | Weinstein et al. |
| 5,947,284 A | 9/1999 | Foster |
| 5,954,369 A | 9/1999 | Seabrook |
| 5,975,295 A | 11/1999 | Diamond |
| 6,004,136 A | 12/1999 | Ehrenpreis |
| 6,012,586 A | 1/2000 | Misra |
| 6,068,121 A | 5/2000 | McGlinch |
| 6,089,943 A | 7/2000 | Lo |
| 6,142,152 A | 11/2000 | Gawarecki |
| 6,158,437 A | 12/2000 | Vagley |
| 6,159,017 A | 12/2000 | Coomansingh |
| D442,697 S | 5/2001 | Hajianpour |
| D450,130 S | 11/2001 | Goldstein |
| D450,391 S | 11/2001 | Hunt et al. |
| 6,330,427 B1 | 12/2001 | Tabachnik |
| 6,361,396 B1 | 3/2002 | Snyder et al. |
| 6,382,212 B1 | 5/2002 | Borchard |
| 6,405,863 B1 | 6/2002 | Dhindsa |
| 6,454,097 B1 | 9/2002 | Blanco |
| 6,579,271 B1 | 6/2003 | Aruffo et al. |
| 6,659,506 B1 | 12/2003 | Erisalu |
| 6,681,933 B1 | 1/2004 | Demsien et al. |
| 6,769,546 B2 | 8/2004 | Busch |
| D495,491 S | 9/2004 | Ramirez |
| 6,793,078 B2 | 9/2004 | Roshdy |
| 6,840,379 B2 | 1/2005 | Franks-Farah et al. |
| 6,896,141 B2 | 5/2005 | McMichael et al. |
| 6,915,901 B2 | 7/2005 | Feinberg |
| 6,926,708 B1 | 8/2005 | Franks-Farah et al. |
| 6,948,742 B2 | 9/2005 | Buck |
| 7,048,120 B2 | 5/2006 | Pond |
| 7,066,328 B2 | 6/2006 | Pulsifer |
| D530,920 S | 10/2006 | Snell |
| D547,064 S | 7/2007 | Snell |
| D549,454 S | 8/2007 | Åhman |
| 7,264,869 B2 | 9/2007 | Tobita |
| 7,278,987 B2 | 10/2007 | Solazzo |
| D557,047 S | 12/2007 | Dretzka |
| D561,473 S | 2/2008 | Phillips et al. |
| D563,673 S | 3/2008 | Dretzka |
| 7,401,703 B2 * | 7/2008 | McMichael ............ A61B 50/33 206/370 |
| 7,434,687 B2 | 10/2008 | Itou et al. |
| D579,662 S | 11/2008 | Dretzka |
| D590,596 S | 4/2009 | Dretzka |
| D596,311 S | 7/2009 | Antons |
| 7,624,869 B2 | 12/2009 | Primer |
| D609,819 S | 2/2010 | Tomes et al. |
| D612,153 S | 3/2010 | Liao |
| 7,785,312 B2 | 8/2010 | Thorne |
| D623,765 S | 9/2010 | Tomes et al. |
| 7,789,873 B2 | 9/2010 | Kubalak |
| D636,894 S | 4/2011 | Tomes et al. |
| D638,137 S | 5/2011 | Gross et al. |
| D650,912 S | 12/2011 | Tomes et al. |
| D662,218 S | 6/2012 | Pittman |

(56) References Cited

U.S. PATENT DOCUMENTS

| | | | |
|---|---|---|---|
| 8,448,786 B2 | 5/2013 | Tomes et al. |
| D688,461 S | 8/2013 | Ambrefe et al. |
| 8,628,549 B2 | 1/2014 | To et al. |
| 8,631,935 B2 | 1/2014 | Tomes et al. |
| 8,678,190 B2 | 3/2014 | Tomes et al. |
| 8,708,999 B2 | 4/2014 | Hong et al. |
| D704,856 S | 5/2014 | Tomes et al. |
| D708,347 S | 7/2014 | Lober |
| D708,759 S | 7/2014 | Heyman et al. |
| D720,470 S | 12/2014 | Lober |
| D720,471 S | 12/2014 | Angel et al. |
| 9,084,593 B2 | 7/2015 | Yakel et al. |
| D742,028 S | 10/2015 | Hutchison |
| 9,283,352 B2 | 3/2016 | Tomes et al. |
| 9,522,753 B2 | 12/2016 | Tomes et al. |
| D779,082 S | 2/2017 | Andre et al. |
| D800,337 S | 10/2017 | Daines |
| 9,795,761 B2 | 10/2017 | Lockwood et al. |
| 9,808,400 B2 | 11/2017 | Tomes et al. |
| D832,456 S | 10/2018 | Self |
| 10,251,812 B2 | 4/2019 | Tomes et al. |
| 10,640,243 B2 | 5/2020 | Tomes et al. |
| 2002/0185406 A1 | 12/2002 | Massengale |
| 2003/0031995 A1 | 2/2003 | Laura |
| 2003/0038475 A1 | 2/2003 | Stancil |
| 2003/0075474 A1 | 4/2003 | Moyer et al. |
| 2003/0159966 A1 | 8/2003 | McMichael et al. |
| 2003/0159969 A1 | 8/2003 | McMichael et al. |
| 2004/0004019 A1 | 1/2004 | Busch |
| 2004/0031721 A1 | 2/2004 | Mann |
| 2004/0055919 A1 | 3/2004 | Rowe et al. |
| 2004/0161732 A1 | 8/2004 | Stump |
| 2004/0180822 A1 | 9/2004 | Grafton |
| 2004/0195145 A1 | 10/2004 | Roshdy |
| 2004/0238391 A1 | 12/2004 | Pond |
| 2005/0022822 A1 | 2/2005 | Santilli |
| 2005/0101905 A1 | 5/2005 | Merry |
| 2005/0228691 A1 | 10/2005 | Paparo |
| 2005/0241986 A1 | 11/2005 | Massengale et al. |
| 2005/0256453 A1 | 11/2005 | Nagamatsu |
| 2005/0285385 A1 | 12/2005 | Bova |
| 2006/0009742 A1 | 1/2006 | Solazzo |
| 2006/0011501 A1 | 1/2006 | Itou |
| 2006/0029912 A1 | 2/2006 | Kearby et al. |
| 2006/0088355 A1 | 4/2006 | Ribi |
| 2006/0096877 A1 | 5/2006 | Khajavi et al. |
| 2006/0186010 A1 | 8/2006 | Warnack |
| 2006/0264822 A1 | 11/2006 | Nagamatsu |
| 2006/0271019 A1 | 11/2006 | Stoller |
| 2007/0026472 A1 | 2/2007 | Prokash et al. |
| 2007/0060908 A1 | 3/2007 | Webster et al. |
| 2007/0065792 A1 | 3/2007 | Schubarth |
| 2007/0084742 A1 | 4/2007 | Miller et al. |
| 2007/0088330 A1 | 4/2007 | House |
| 2007/0095699 A1 | 5/2007 | Frieze |
| 2007/0142786 A1 | 6/2007 | Lampropoulos |
| 2007/0161971 A1 | 7/2007 | House |
| 2007/0203464 A1 | 8/2007 | Green et al. |
| 2007/0225687 A1 | 9/2007 | House |
| 2007/0299431 A1 | 12/2007 | Jakubowski et al. |
| 2008/0116106 A1 | 5/2008 | Lampropoulos et al. |
| 2008/0121553 A1 | 5/2008 | Gobel |
| 2008/0221515 A1 | 9/2008 | Nagamatsu |
| 2008/0249476 A1 | 10/2008 | Bierman et al. |
| 2008/0281254 A1 | 11/2008 | Humayun et al. |
| 2008/0283426 A1 | 11/2008 | Primer et al. |
| 2008/0283433 A1 | 11/2008 | Primer |
| 2009/0004055 A1 | 1/2009 | Darrigrand et al. |
| 2009/0071854 A1 | 3/2009 | Martin |
| 2009/0099531 A1 | 4/2009 | Griesbach, III |
| 2009/0152160 A1 | 6/2009 | Thompson et al. |
| 2009/0184026 A1 | 7/2009 | Massengale et al. |
| 2009/0194453 A1 | 8/2009 | Thorne et al. |
| 2009/0234346 A1 | 9/2009 | McBride et al. |
| 2009/0236259 A1 | 9/2009 | Hicks |
| 2009/0318783 A1 | 12/2009 | Rohde et al. |
| 2010/0274205 A1 | 10/2010 | Morelli et al. |
| 2010/0307941 A1 | 12/2010 | Tomes et al. |
| 2010/0307942 A1 | 12/2010 | Tomes et al. |
| 2010/0311026 A1 | 12/2010 | Tomes et al. |
| 2011/0107494 A1 | 5/2011 | Haines |
| 2011/0155599 A1 | 6/2011 | Yakel et al. |
| 2011/0232234 A1 | 9/2011 | Lockwood et al. |
| 2011/0233079 A1 | 9/2011 | Macinnes et al. |
| 2011/0284410 A1 | 11/2011 | Lockwood |
| 2011/0290260 A1 | 12/2011 | Tomes et al. |
| 2011/0290262 A1 | 12/2011 | Tomes et al. |
| 2011/0297147 A1 | 12/2011 | Lick et al. |
| 2012/0145589 A1 | 6/2012 | Macinnes et al. |
| 2014/0110296 A1 | 4/2014 | Terzibashian |
| 2017/0202699 A1* | 7/2017 | Zani ............... B65D 33/004 |
| 2017/0216558 A1* | 8/2017 | Hughett ............ A61F 13/38 |
| 2017/0368302 A1* | 12/2017 | Brooks ............. A61B 42/10 |
| 2019/0344044 A1 | 11/2019 | Dickinson et al. |

FOREIGN PATENT DOCUMENTS

| | | |
|---|---|---|
| EP | 2007/045943 | 4/2007 |
| JP | 2007-229520 | 9/2007 |
| WO | 2005/027767 | 3/2005 |
| WO | 2006/114466 | 11/2006 |
| WO | 2007/045943 | 4/2007 |

OTHER PUBLICATIONS

Chinese Application No. 201280035240.4; Filed May 24, 2012; dated Aug. 18, 2015.

Dictionary definition m-w. URL:<http://ww.merriam-webster.com/dictionary/reassure>. Retrieved from Internet Dec. 10, 2013.

Dictionary definition m-w. URL:<http://www.merriam-webster.com/dictionary/brave>. Retrieved fro Internet Dec. 10, 2013.

Dover Intermittent Catheter Tray—14 fr, Red Rubber; Website http://tinyurl.com/o4esnivh; Unknown Publication Date.

Inter Partes Review—Patent Owner's Prelim. Response; U.S. Pat. No. 9,795,761; Inter Partes Review No. IPR2019-00109; Filed Feb. 22, 2019.

Inter Partes Review—Patent Owner's Prelim. Response; U.S. Pat. No. 9,808,400; Inter Partes Review No. IPR2019-00208; Filed Mar. 7, 2019.

IPR Petition 2001, Declaration of Meyst dated Jan. 11, 2019; IPR 2019-00035, IPR-2019-00036.

IPR Petition 2002, Declaration of Weintraub dated Jan. 11, 2019; IPR 2019-00035, IPR-2019-00036.

IPR Petition Exhibit 2001, Declaration of Meyst dated Feb. 22, 2019; IPR2019-00109.

IPR Petition Exhibit 2001, Declaration of Meyst dated Mar. 7, 2019; IPR2019-00208.

IPR Petition Exhibit 2001; Declaration of Meyst dated Mar. 7, 2019; IPR2019-00223.

IPR Petition Exhibit 2002, Declaration of Weintraub dated Mar. 7, 2019; IPR2019-00208.

IPR Petition Exhibit 2002, Declaration of Weintraub dated Mar. 7, 2019; IPR2019-00223.

Lion King Sticker website. URL: <http://tlkobession.wuffpaws.org/OldSite/games/games2.html>. 1996 Retrieved from Internet Dec. 10, 2013.

Lion Sticker Activity Book website. URL: <http://www.amazon.com/Disneys-Simbas-Pride-Sticker-Activity/dp/B0018DOJZA>. 1998 Retrieved from Internet Dec. 10, 2013.

*Medline Industries inc* vs *C.R Bard, Inc.*, Exhibit 1 to Declaration of Karl L. Leinsing in Support of Bard's Rebuttal on Claim Construction; Civil Action No. 1:16-cv-03529; Judge Sharon Johnson Coleman; Filed Jan. 12, 2018.

*Medline Industries inc* vs *C.R Bard, Inc.*. Exhibit A to Declaration of Bnan Eutermoser in Support of Medline Response to Bard Opening Claim Construction; Civil Action No. 1:16-cv-03529; Judge Sharon Johnson Coleman; Filed Dec. 9, 2016.

(56) References Cited

OTHER PUBLICATIONS

*Medline Industries Inc* vs *C.R Bard, Inc.*. Exhibit A to Declaration of Dylan J Raife in Support of Bard's Reply Claim Construction Brief; Civil Action No. 1:14-cv-03618: Judge John Z. Lee; Filed Aug. 15, 2016.
*Medline Industries Inc* vs *C.R Bard, Inc*: Exhibit F to C.R. Bard's LPR 2.3 Contentions; Civil Action No. 1.17-cv-7216; Judge Sara L. Ellis; Filed Jan. 16, 2018.
*Medline Industries inc* vs *C.R Bard, Inc.*, Exhibit 4 to Declaration of Richard Meyst re Claim Construction; Civil Action No. 1:16-cv-03529: Judge Sharon Johnson Coleman; Filed Dec. 9, 2016.
*Medline Industries Inc* vs *C.R Bard, Inc.*, Exhibit C to Declaration of Nicole Smith in Support of Bard Reply to Claim Construction Brief; Civil Action No. 1.16-cv-03529; Judge Sharon Johnson Coleman. Filed Jan. 12, 2018.
*Medline Industries inc* vs *C.R Bard, Inc.*. Exhibit 3 to Declaration of Richard Meyst re Claim Construction; Civil Action No. 1:16-cv-03529: Judge Sharon Johnson Coleman. Filed Dec. 9, 2016.
*Medline Industries Inc* vs *C.R Bard. Inc.*; Exhibit C to Declaration of Nicole Smith in Support of Bard Reply to Medline Claim Construction Brief; Civil Action No. 116-cv-03529; Judge Sharon Johnson Coleman; Filed Jan. 27, 2017.
*Medline Industries Inc* vs *C.R Bard. Inc.*; Exhibit F to Declaration of Brian Eutermoser in Support of Medline Response to Bard Opening Claim Construction; Civil Action No. 1:16-cv-03529; Judge Sharon Johnson Coleman: Filed Dec. 9, 2016.
*Medline Industries Inc* vs *C.R. Bard, Inc.*; Exhibit E to Declaration of Nicole Smith in Support of Bard Reply to Claim Construction Brief; Civil Action No. 1.16-cv-03529. Judge Sharon Johnson Coleman. Filed Jan. 12, 2018.
*Medline Industries Inc* vs *C.R Bard, Inc*; Exhibit A (List of Invalidating Prior Art) to C R. Bard's LPR 2 3 Contentions; Civil Action No. 1:17-cv-7216; Judge Sara L. Ellis; Filed Jan. 16, 2018.
*Medline Industries inc.* vs *C R. Bard, Inc*; Exhibit E to Declaration of Dylan Raife in Support of Motion for Leave to Add Counter-claims; Civil Action No. 1:17-cv-7216; Judge Sara L. Ellis; Filed Feb. 27, 2018.
*Medline industnes Inc,* vs*C.R Bard, Inc.*; Exhibit A to Declaration of Nicole M. Smith; Civil Action No. 1:14-cv-03618; Judge John Z. Lee: Filed Jun. 4, 2016.
*Medline industnes Inc.* vs *C R. Bard, Inc*; C.R Bard's LPR 2 3 Contentions; Civil Action No. 1:17-cv-7216, Judge Sara L. Ellis; Filed Jan. 16, 2018.
*Medline Industnes Inc.* vs *C R. Bard, Inc*; Declaration of Nicole M Smith in Support of Bard Opening Claim Construction Brief; Civil Action No. 1:14-cv-03618: Judge John Z. Lee; Filed Jun. 4, 2016.
*Medline industnes Inc.* vs *C R. Bard, Inc*; Exhibit B to Declaration of Dylan Raife in Support of Motion for Leave to Add Counter-claims; Civil Action No. 1:17-cv7216; Judge Sara L. Ellis; Filed Feb. 27, 2018.
*Medline Industnes inc.* vs *C R. Bard, Inc*; Exhibit D to Declaration of Dylan Raife in Support of Motion for Leave to Add CounterClaims; Civil Action No. 1:17-cv-7216; Judge Sara L. Ellis: Filed Feb. 27, 2018.
*Medline Industnes Inc.* vs *C.R Bard, Inc.*; Exhibit G to Declaration of Nicole M. Smith; Civil Action No. 1:14-cv-03618; Judge John Z, Lee; Filed Jun. 4, 2016.
*Medline Industnes Inc.* vs *C.R Bard, Inc.*; Exhibit H to Declaration of Nicole M. Smith; Civil Action No. 1:14-cv-03618; Judge John Z. Lee; Filed Jun. 4, 2016.
*Medline Industnes Inc.* vs*C R. Bard, inc*; Exhibit A-C R. Bards Second Amended Answer to Second Amended Complaint: Civil Action No. 1:17-cv-7216; Judge Sara L Ellis; Filed Feb. 27, 2018.
*Medline Industries Inc* vs *C.R Bard, Inc.*, Declaration of Barbara Weintraub re Claim Conslruction; Civil Action No. 1:16-cv-03529; Judge Sharon Johnson Coleman; Filed Dec. 22, 2017.
*Medline industries Inc* vs *C.R Bard, Inc.*, Declaration of Dylan J Raife in Support of Bard Opening Claim Construction Brief; Civil Action No. 1:16-cv-03529; Judge Sharon Johnson Coleman; Filed Nov. 17, 2017.
*Medline Industries Inc* vs *C.R Bard, Inc.*, Declaration of Nicole Smith in Support of Bard Reply to Medline Claim Construction Brief; Civil Action No. 1:16-cv-03529; Judge Sharon Johnson Coleman; Filed Jan. 27, 2017.
*Medline Industries Inc* vs *C.R Bard, Inc.*, Exhibit 1 to Declaration ol Richard Meyst re Claim Construction; Civil Action No. 1:16-cv-03529; Judge Sharon Johnson Coleman; Filed Dec. 9, 2016.
*Medline Industries inc* vs *C.R Bard, Inc.*, Exhibit 2 to Declaration ol Richard Meyst re Claim Construction; Civil Action No. 1:16-cv-03529; Judge Sharon Johnson Coleman; Filed Dec. 9, 2016.
*Medline Industries Inc* vs *C.R Bard, Inc.*, Exhibit 7 to Declaration of Richard Meyst Regarding Claim Construction: Civil Action No. 1:14-cv-03618; Judge John Z. Lee; Filed Jul. 8, 2016.
*Medline Industries Inc* vs *C.R Bard, Inc.*, Exhibit A to Declaration of Dylan J Raife in Support of Bard Opening Claim Construction Brief; Civil Action No. 1;16-cv-03529; Judge Sharon Johnson Coleman; Filed Nov. 11, 2016.
*Medline Industries Inc* vs *C.R Bard, Inc.*, Exhibit A to Declaration of Kevin A. Lake. Civil Action No. 1:14-cv-03618; Judge John Z. Lee; Filed Jul. 8, 2016.
*Medline Industries Inc* vs *C.R Bard, Inc.*, Exhibit B to Declaration of Brian Eutermoser in Support of Medline Response to Bard Opening Claim Construction; Civil Action No. 1:16-cv-03529: Judge Sharon Johnson Coleman: Filed Dec. 9, 2016.
*Medline Industries inc* vs *C.R Bard, inc.*, Exhibit F to Declaration of Dyian J. Raife in Support of Bard Opening Claim Construction Brief, Civil Action No. 1:16-cv-03529; Judge Sharon Johnson Coleman; Filed Nov. 11, 2016.
*Medline Industries Inc* vs *C.R Bard, Inc.*, Exhibit F to Declaration of Nicole Smith in Support of Bard Reply to Medline Claim Construction Brief; Civil Action No. 1:16-cv-03529; Judge Sharon Johnson Coleman; Filed Jan. 27, 2017.
*Medline Industries inc* vs *C.R Bard, Inc.*, Exhibit H to Declaration of Kevin A. Lake; Civil Action No. 1:14-cv-03618: Judge John Z. Lee; Filed Jul. 8, 2016.
*Medline Industries Inc* vs *C.R Bard, Inc.*. Bard Opening Claim Construction Brief; Civil Action No. 1" 16-cv-03529; Judge Sharon Johnson Coleman; Filed Nov. 11, 2016.
*Medline Industries Inc* vs *C.R Bard, Inc.*. Declaration of Dylan J Raife in Support of Bard's Reply Claim Construction Brief: Civil Action No. I:14-cv-03518; Judge John Z. Lee; Fiied Aug. 15, 2016.
*Medline Industries Inc* vs *C.R Bard, Inc.*. Exhibit 1 to Declaration of Dylan J. Raife in Support of Bard Opening Claim Construction Brief; Civil Action No. 1:16-cv-03529; Judge Sharon Johnson Coleman; Filed Nov. 11, 2016.
*Medline Industries Inc* vs *C.R Bard, Inc.*. Exhibit 10 to Declaration of Richard Meyst Regarding Claim Construction: Civil Action No. 1:14-cv-03618; Judge John Z. Lee; Filed Jul. 8, 2016.
*Medline Industries Inc* vs *C.R Bard, Inc.*. Exhibit 2 to Declaration of Brian Eutermoser in Support of Medline Surrepiy: Civil Action No. 1:14-cv-03618; Judge John Z. Lee; Filed Sep. 7, 2016.
*Medline Industries Inc* vs *C.R Bard, Inc.*. Exhibit C to Declaration of Dylan J Raife in Support of Bard Opening Claim Construction Brief; Civil Action No. 1:16-cv-03529; Judge Sharon Johnson Coleman: Filed Nov. 11, 2016.
*Medline Industries Inc* vs *C.R Bard, Inc.*. Exhibit E to Declaration of Nicole Smith in Support of Bard Reply to Medline Claim Construction Brief; Civil Action No. 1:16-cv-03529; Judge Sharon Johnson Coleman; Filed Jan. 27, 2017.
*Medline Industries inc* vs *C.R Bard, Inc.*. Exhibit I to Declaration of Brian Eutermoser in Support of Medline Response to Bard Opening Claim Construction; Civil Action No. 1:16-cv-03529; Judge Sharon Johnson Coleman; Filed Dec. 9, 2016.
*Medline Industries Inc* vs *C.R Bard, Inc.*. Exhibit i to Declaration of Nicoie M. Smith, Civil Action No. 1:14-cv-03618: Judge John Z. Lee; Filed Jun. 4, 2016.
*Medline Industries Inc* vs *C.R Bard, Inc.*; Bard Reply to Medline Claim Construction Brief; Civil Action No. 1 16-cv-03529; Judge Sharon Johnson Coleman; Filed Jan. 27, 2017.
*Medline Industries Inc* vs *C.R Bard, Inc.*; C. R. Bard's Reply in Support of Claim Construction Brief; Civii Action No. 1.14-cv-03618, Judge John Z. Lee; Filed Aug. 15, 2016.

(56) References Cited

OTHER PUBLICATIONS

*Medline Industries Inc* vs *C.R Bard, Inc.*; Declaration of Karl L Leinsing in Support of Bard's Rebuttal on Claim Construction; Civil Action No. 1:16-CV-03529; Judge Sharon Johnson Coleman; Filed Jan. 12, 2018.

*Medline Industries inc* vs *C.R Bard, Inc.*; Declaration of Karl L. Leinsing in Support of Bard's Rebuttal on Claim Construction; Civil Action No. 1.14-cv-03618. Judge John Z. Lee; Filed Aug. 15, 2016.

*Medline Industries Inc* vs *C.R Bard, Inc.*; Declaration of Richard Meyst re Claim Construction; Civil Action No. 1.16-cv-03529. Judge Sharon Johnson Coleman; Filed Dec. 9, 2016.

*Medline Industries Inc* vs *C.R Bard, Inc.*; Exhibit 1 to Declaration of Karl L Leinsing in Support of Bard's Rebuttal on Claim Construction; Civil Action No. 1.14-cv-03618; Judge John Z. Lee, Filed Aug. 15, P016.

*Medline Industries Inc* vs *C.R Bard, Inc.*; Exhibit 1 to Declaration of Karl R Leinsing in Support of Bard Reply to Medline Claim Construction Brief; Civil Action No. 1:16-cv-03529; Judge Sharon Johnson Coleman; Filed Jan. 27, 2017.

*Medline Industries Inc* vs *C.R Bard, Inc.*; Exhibit 3 to Declaration of Richard Meyst Regarding Claim Construction; Civil Action No. 1:14-cv-03618; Judge John Z. Lee, Filed Jul. 8, 2016.

*Medline Industries inc* vs *C.R Bard, Inc.*; Exhibit 4 to Declaration of Richard Meyst Regarding Claim Construction; Civil Action No. 1:14-cv-03618; Judge John Z. Lee. Filed Jul. 8, 2016.

*Medline Industries inc* vs *C.R Bard, Inc.*; Exhibit A to Declaration of Barbara Weintraub re Claim Construction; Civil Action No. 1:16-cv-03529; Judge Sharon Johnson Coleman. Filed Dec. 9, 2016.

*Medline Industries Inc* vs *C.R Bard, Inc.*; Exhibit B to Declaration of Nicole Smith in Support of Bard Reply to Claim Construction Brief; Civil Action No. 1;16-cv-03529. Judge Sharon Johnson Coleman. Filed Jan. 12, 2018.

*Medline Industries Inc* vs *C.R Bard, Inc.*; Exhibit B to Declaration of Dylan J Raife in Support of Bard's Reply Claim Construction Brief; Civil Action No. 1:14-cv-03618; Judge John Z. Lee; Filed Aug. 15, 2016.

*Medline Industries Inc* vs *C.R Bard, Inc.*; Exhibit C to Declaration of Dylan J Raife in Support of Bard's Reply Claim Construction Brief; Civil Action No. 1:14-cv 03618; Judge John Z. Lee; Filed Aug. 15, 2016.

*Medline Industries Inc* vs *C.R Bard, Inc.*; Exhibit D to Declaration of Brian Eutermoser in Support of Medline Response to Bard Opening Claim Construction; Civil Action No. 1:16-cv-03529; Judge Sharon Johnson Coleman; Filed Dec. 9, 2016.

*Medline Industries Inc* vs *C.R Bard, Inc.*; Exhibit D to Declaration of Dylan J Raife in Support of Bard's Reply Claim Construction Brief: Civil Action No. 1.14-cv-03618; Judge John Z. Lee. Filed Aug. 15. 2016.

*Medline Industries Inc* vs *C.R Bard, Inc.*; Exhibit D to Declaration of Nicole Smith in Support of Bard Reply to Medline Claim Construction Brief; Civil Action No. 1.16-cv-03529; Judge Sharon Johnson Coleman; Filed Jan. 27, 2017.

*Medline Industries Inc* vs *C.R Bard, Inc.*; Exhibit E to Declaration of Kevin A. Lake; Civil Action No. 1:14-cv-03618, Judge John Z. Lee; Filed Jul. 8, 2016.

*Medline Industries inc* vs *C.R Bard, Inc.*; Exhibit F to Declaration of Kevin A Lake: Civil Action no. 1:14-cv-03618. Judge John Z. Lee; Filed Jul. 8, 2016.

*Medline Industries Inc* vs *C.R Bard, Inc.*; Exhibit F to Declaration of Dylan J. Raife in Support ol Bard's Reply Claim Construction Brief; Civil Action No. 1. I4-cv-03618; Judge John Z. Lee, Filed Aug. 15, 2016.

*Medline Industries inc* vs *C.R Bard, Inc.*; Exhibit G to Declaration of Kevin A. Lake; Civil Action No. 1:14-cv-03618. Judge John Z. Lee; Filed Jul. 8, 2016.

*Medline Industries Inc* vs *C.R Bard, Inc.*; Exhibit G to Declaration of Nicole Smith in Support ol Bard Reply to Medline Claim Construction Brief: Civil Action No. 1:16-cv-03529: Judge Sharon Johnson Coleman; Filed Jan. 27, 2017.

*Medline Industries Inc* vs *C.R Bard, Inc.*; Exhibit H to Declaration of Bnan Eutermoser in Support of Medline Response to Bard Opening Claim Construction; Civil Action No. 1:16-cv-03529; Judge Sharon Johnson Coleman; Filed Dec. 9, 2016.

*Medline Industries Inc* vs *C.R Bard, Inc.*; Exhibit H to Declaration of Dylan J. Raife in Support of Bard Opening Claim Construction Brief. Civil Action Mo. 1:16-cv-Q3529; Judge Sharon Johnson Coleman; Filed Nov. 11, 2016.

*Medline Industries Inc* vs *C.R Bard, Inc.*; Exhibit I to Declaration of Kevin A. Lake; Civil Action No. 1.14-sv-03618; Judge John Z. Lee; Filed Jul. 8, 2016.

*Medline Industries Inc* vs *C.R Bard, Inc.*; Exhibit N to Declaration of Brian Eutermoser in Support of Medline Response to Bard Opening Claim Construction; Civil Action No. 1:16-cv-03529; Judge Sharon Johnson Coleman; Filed Dec. 9, 2016.

*Medline Industries Inc* vs *C.R Bard, Inc.*; Medline Memo of Law re Expert Testimony in Claim Construction Proceedings; Civil Action No. 1;14-cv-03618; Judge John Z. Lee. Filed Jan. 25, 2017.

*Medline Industries Inc* vs *C.R Bard, Inc.*; Medline Surreply to Claim Construction Brief; Civil Action No. 1.14-CV-Q3618: Judge John Z. Lee; Filed Sep. 7, 2016.

*Medline Industries Inc* vs *C.R Bard, Inc.*; Transcript of Deposition of Richard Meyst; Civil Action No. 1:16-W-03529. Jan. 20, 2017.

*Medline Industries Inc* vs *C.R Bard, Inc*: Exhibit G to C.R Bard's LPR 2.3 Contentions; Civil Action No. 1.17-cv-7216; Judge Sara L Ellis; Fiied Jan. 16, 2013.

*Medline Industries inc* vs *C.R Bard, Inc*; Exhibit 3 to C.R. Bard's LPR 2.3 Contentions; Civil Action No. 1:17-CV-7216; Judge Sara L Ellis; Filed Jan. 16, 2018.

*Medline Industries Inc* vs *C.R Bard, Inc*; Exhibit C to C.R. Bard's LPR 2.3 Contentions; Civil Action No. 1:17-cv-7216; Judge Sara L. Ellis; Filed Jan. 16, 2018.

*Medline Industries Inc* vs *C.R Bard, Inc*; Exhibit D to C.R. Bard's LPR 2.3 Contentions; Civil Action No. 1:17-cv-7216; Judge Sara L. Etlis; Filed Jan. 16, 2018.

*Medline Industries Inc* vs *C.R Bard, Inc*; Exhibit E to C R. Bard's LPR 2.3 Contentions; Civil Action No. 1;17-cv-7216; Judge Sara L. Ellis; Fiied Jan. 16, 2018.

*Medline Industries Inc* vs *C.R Bard, Inc*, Exhibit H loC.R. Bard's LPR 2.3 Contentions. Civil Action No. 1:17-CV-7216; Judge Sara L. Ellis: Filed Jan. 16, 2018.

*Medline industries Inc* vs *C.R Bard, Inc.*, Declaration of Bnan Eutermoser in Support of Medline Surreply. Civil Action No. 1:14-cv-03618, Judge John Z. Lee; Filed Sep. 7, 2016.

*Medline Industries Inc* vs *C.R Bard, Inc.*, Exhibit 8 to Declaration of Richard Meyst Regarding Claim Construction: Civil Action No. 1:14-cv-03618: Judge John Z. Lee: Filed Jul. 8, 2016.

*Medline Industries Inc* vs *C.R Bard, Inc.*, Exhibit A to Declaration of Barbara Weintraub Regarding Claim Construction: Civil Action No. 1.14-cv-03618. Judge John Z. Lee; Filed Jul. 8, 2016.

*Medline Industries Inc* vs *C.R Bard, Inc.*, Exhibit A to Declaration of Nicole Smith in Support of Bard Repiy to Medline Claim Construction Brief; Civil Action No. 1.16-cv-03529; Judge Sharon Johnson Coleman; Filed Jan. 27, 2017.

*Medline Industries Inc* vs *C.R Bard. Inc.*, Exhibit B to Declaration of Dylan J Raife in Support of Bard Opening Claim Construction Brief; Civil Action No. 1:16-cv-03529; Judge Sharon Johnson Coleman; Filed Nov. 11, 2016.

*Medline Industries Inc* vs *C.R Bard. Inc.*, Exhibit E to Declaration of Dylan J Raife in Support of Bard's Reply Claim Construction Brief; Civil Action No. 1.14-cv-03618; Judge John Z. Lee, Filed Aug. 15, 2016,.

*Medline Industries inc* vs *C.R Bard. Inc.*. Declaration of Richard Meyst Regarding Claim Construction; Civil Action No. 1:14-cv-03618; Judge John Z. Lee; Filed Jul. 8, 2016.

*Medline Industries Inc* vs *C.R Bard. Inc.*. Exhibit 11 to Declaration of Richard Meyst re Claim Construction: Civil Action No. 1:16-cv-03529; Judge Sharon Johnson Coleman; Filed Dec. 9, 2016.

*Medline Industries inc* vs *C.R Bard. Inc.*. Exhibit A to Declaration of Richard Meyst Regarding Claim Construction; Civil Action No. 1;14-cv-03618; Judge John Z. Lee; Filed Jul. 8, 2016.

(56) References Cited

OTHER PUBLICATIONS

*Medline Industries Inc* vs *C.R Bard. Inc.*. Medline Motion to Supplement Record on Claim Construction with Leinsing Testimony; Civil Action No. 1:14-w-03618; Judge John Z. Lee; Filed Mar. 23, 2017.
*Medline Industries Inc* vs *C.R Bard. Inc.*; Bard Reply Claim Construction Brief; Civil Action No. 1:16-cv-03529; Judge Sharon Johnson Coleman; Filed Jan. 12, 2018.
*Medline Industries Inc* vs *C.R Bard. Inc.*; Bard Response to Memo of Law re Expert Testimony in Claim Construction Proceedings; Civil Action No. 1:14-cv-03618; Judge John Z. Lee. Filed Feb. 8, 2017.
*Medline Industries Inc* vs *C.R Bard. Inc.*; Declaration of Brian Eutermoser in Support of Medline Response to Bard Opening Claim Construction Brief. Civil Action No. 1:16-cv-03529; Judge Sharon Johnson Coleman; Filed Dec. 22, 2017.
*Medline Industries Inc* vs *C.R Bard. Inc.*; Declaration of Karl R. leinsing in Support of Bard Reply to Medline Claim Construction Brief; Civil Action No. 1:16-cv-03529; Judge Sharon Johnson Coleman; Filed Jan. 27, 2017.
*Medline Industries Inc* vs *C.R Bard. Inc.*; Exhibit 3 to Declaration ol Peter Sauer in Support of Medline's Motion to Supplement Record; Civil Action No. 1:14-cv-03618: Judge John Z. Lee. Filed Mar. 23, 2017.
*Medline Industries inc* vs *C.R Bard. Inc.*; Exhibit 8 to Declaration of Richard Meyst re Claim Construction; Civil Action No. 1:16-cv-03529; Judge Sharon Johnson Coleman; Filed Dec. 9, 2016.
*Medline Industries Inc* vs *C.R Bard. Inc.*; Exhibit C to Declaration of Kevin A. Lake; Civil Action No. 1 14-cv-03618. Judge John Z. Lee; Filed Jul. 8, 2016.
*Medline Industries Inc* vs *C.R Bard. Inc.*; Exhibit G to Declaration of Dylan J. Raife in Support of Bard Opening Claim Construction Brief, Civil Action No. 1:16-cv-03529; Judge Sharon Johnson Coleman; Filed Nov. 17, 2017.
*Medline Industries Inc* vs *C.R Bard. Inc.*; Exhibit G to Declaration ol Brian Eutermoser in Support of Medline Response to Bard Opening Claim Construction; Civil Action No. 1:16-cv-03529; Judge Sharon Johnson Coleman; Filed Dec. 9, 2016.
*Medline industries Inc* vs *C.R Bard. Inc.*; Exhibit H to Declaration of Dylan J Raife in Support of Bard Opening Claim Construction Brief, Civil Action No. 1:16-cv-03529; Judge Sharon Johnson Coleman; Filed Nov. 17, 2017.
*Medline Industries Inc* vs *C.R Bard. Inc.*; Medline Response to Bard Opening Claim Construction; Civil Action No. 1:16-cv-03529; Judge Sharon Johnson Coleman; Filed Dec. 2016.
*Medline Industries Inc* vs *C.R Bard. Inc.*; Transcript of Deposition of Barbara A Weinlraub; Civil Action Mo. 1:16-cv-03529; Jan. 20, 2017.
*Medline Industries Inc* vs *C.R Bard. Inc.*; Transcript ol Deposition of Karl Leinsing; Civil Action No. 1:16-cv-03529; Feb. 17, 2017.
*Medline industries Inc* vs *C.R Bard. Inc.*; Exhibit 9 to Declaration of Richard Meyst re Claim Construction; Civil Action No. 1:16-cv-03529; Judge Sharon Johnson Coleman; Filed Dec. 9, 2016.
*Medline Industries Inc* vs *C.R. Bard. Inc.*, Bard Response to Medline Surreply re Claim Construction; Civil Action No. 1:14-cv-03618; Judge John Z. Lee; Filed Sep. 13, 2016.
*Medline Industries Inc* vs *C.R. Bard. Inc.*, Exhibit 2 to Declaration ol Karl L. Lansing in Support of Bard's Rebuttal on Claim Construction: Civil Action No. 1:14-cv-03618; Judge John Z. Lee; Filed Aug. 15, 2016.
*Medline Industries Inc* vs *C.R. Bard. Inc.*, Exhibit B to Declaration of Kevin A. Lake. Civil Action No. 1:14-cv-03618; Judge John Z. Lee; Filed Jul. 8, 2016.
*Medline Industries Inc* vs *C.R. Bard. Inc.*, Exhibit D to Declaration of Nicole Smith in Support of Bard Reply to Claim Construction Brief; Civil Action No. 116-cv-03529; Judge Sharon Johnson Coleman. Filed Jan. 12, 2018.
*Medline Industries Inc* vs *C.R. Bard. Inc.*, Exhibit J to Declaration of Brian Eutermoser in Support of Medline Response to Bard Opening Claim Construction; Civii Action No. 1:16-cv-03529: Judge Sharon Johnson Coleman; Filed Dec. 9, 2016.
*Medline Industries inc* vs *C.R. Bard. Inc.*, Exhibit K to Declaration of Bnan Eutermoser in Support of Medline Response to Bard Opening Claim Construction; Civii Action No. 1:16-cv-03529: Judge Sharon Johnson Coleman; Filed Dec. 9, 2016.
*Medline Industries inc* vs *C.R. Bard. Inc.*, Exhibit 1 to Declaration of Peter Sauer in Support of Medline's Motion to Supplement Record; Civil Action No. 1:14-cv-03618; Judge John Z. Lee; Filed Mar. 23, 2017.
*Medline Industries Inc* vs *C.R. Bard. Inc.*. Exhibit 9 to Declaration of Richard Meyst Regarding Claim Construction; Civil Action No. 1:14-cv-03618; Judge John Z. Lee; Filed Jul. 8, 2016.
*Medline Industries Inc* vs *C.R. Bard. Inc.*. Exhibit L to Declaration of Brian Eutermoser in Support of Medline Response to Bard Opening Claim Construction; Civil Action No. 1:16-cv-03529: Judge Sharon Johnson Coleman: Filed Dec. 9, 2016.
*Medline Industries inc* vs *C.R. Bard. Inc.*. Medline Response to Bard Claim Construction Brief. Civil Action No. 1:14--cv-03618: Judge John Z. Lee; Filed Jul. 8, 2016.
*Medline Industries Inc* vs *C.R. Bard. Inc.*: Exhibit 2 to C.R. Bard's LPR 2.3 Contentions; Civil Action No. 117-CV-7216; Judge Sara L Eiiis; Filed Jan. 16, 2018.
*Medline Industries Inc* vs *C.R. Bard. Inc.*; Declaration of Barbara Weintraub re Claim Construction: Civil Action No. 1.16-cv-03529. Judge Sharon Johnson Coleman; Filed Dec. 9, 2016.
*Medline Industries Inc* vs *C.R. Bard. Inc.*; Declaration of Brian Eutermoser in Support of Medline Response to Bard Opening Claim Construction; Civil Action No. 1:16-cv-03529; Judge Sharon Johnson Coleman; Filed Dec. 9, 2016.
*Medline Industries Inc* vs *C.R. Bard. Inc.*; Declaration of Nicole Smith in Support of Bard Reply to Claim Construction Brief; Civil Action No. I:16-cv-03529; Judge Sharon Johnson Coleman; Filed Jan. 12, 2018.
*Medline Industries Inc* vs *C.R. Bard. Inc.*; Exhibit 10 to Declaration of Richard Meyst re Claim Construction; Civil Action No. 1:16-cv-03529; Judge Sharon Johnson Coleman; Filed Dec. 9, 2016.
*Medline Industries Inc* vs *C.R. Bard. Inc.*; Exhibit 2 to Declaration of Peter Sauer in Support of Medline's Motion to Supplement Record; Civil Action No. 1:14-cv-03618; Judge John Z. Lee. Filed Mar. 23, 2017.
*Medline Industries Inc* vs *C.R. Bard. Inc.*; Exhibit 5 to Declaration of Richard Meyst re Claim Construction: Civil Action No. 1:16-cv-03529; Judge Sharon Johnson Coleman, Filed Dec. 9, 2016.
*Medline Industries Inc* vs *C.R. Bard. Inc.*; Exhibit 6 to Declaration of Richard Meyst re Claim Construction; Civil Action No. 1:16-cv-03529; Judge Sharon Johnson Coleman. Filed Dec. 9, 2016.
*Medline industries inc* vs *C.R. Bard. Inc.*; Exhibit 7 to Declaration of Richard Meyst re Claim Construction; Civil Action No. 1:16-cv-03529; Judge Sharon Johnson Coleman; Filed Dec. 9, 2016.
*Medline Industries inc* vs *C.R. Bard. Inc.*; Exhibit C to Declaration of Bnan Eutermoser in Support of Medline Response to Bard Opening Claim Construction; Civil Action No. 1:16-cv-03529; Judge Sharon Johnson Coleman; Filed Dec. 9, 2016.
*Medline Industries inc* vs *C.R. Bard. Inc.*; Exhibit E to Declaration of Brian Eutermoser in Support of Medline Response to Bard Opening Claim Construction; Civil Action No. 1:16-cv-03529; Judge Sharon Johnson Coleman; Filed Dec. 9, 2016.
*Medline Industries Inc* vs *C.R. Bard. Inc.*; Exhibit M to Declaration of Brian Eutermoser in Support of Medline Response to Bard Opening Claim Construction; Civil Action No. 1:16-cv-03529; Judge Sharon Johnson Coleman; Filed Dec. 9, 2016.
*Medline Industries Inc* vs *C.R. Bard. Inc.*; Exhibit 2 to Declaration of Richard Meyst Regarding Claim Construction: Civil Action No. 1:14-cv-03618; Judge John Z. Lee. Filed Jul. 8, 2016.
*Medline Industries Inc* vs *C.R. Bard. Inc.*; Exhibit 5 to Declaration of Richard Meyst Regarding Claim Construction; Civil Action No. 1:14-cv-03618; Judge John Z. Lee. Filed Jul. 8, 2016.
*Medline Industries Inc* vs *C.R. Bard. Inc.*; Exhibit 6 to Declaration of Richard Meyst Regarding Claim Construction; Civil Action No. 1:14-cv-03618; Judge John Z. Lee. Filed Jul. 8, 2016.

(56) References Cited

OTHER PUBLICATIONS

*Medline Industries inc* vs *C.R. Bard. Inc.*; Medline Response to Bard Opening Claim Construction Brief; Civil Action No. 1:16-cv-03529; Judge Sharon Johnson Coleman; Filed Dec. 22, 2017.
*Medline Industries Inc* vs *C.R. Bard. Inc.*; Exhibit E to Declaration of Dylan J Raife in Support of Bard Opening Claim Construction Brief; Civil Action No. 1:16-cv-03529; Judge Sharon Johnson Coleman; Filed Nov. 11, 2016.
*Medline Industries Inc* vs*C.R Bard. Inc*, Exhibit Ito C.R. Bard's LPR 2.3 Contentions. Civil Action No. 1:17-cv-7216; Judge Sara L. Ellis; Filed Jan. 16, 2018.
*Medline Industries Inc* vs*C.R Bard. Inc.*, Declaration of Dylan J Raife in Support of Bard Opening Claim Construction Brief; Civil Action No. 1:16-cv-03529; Judge Sharon Johnson Coleman; Filed Nov. 11, 2016.
*Medline Industries Inc* vs*C.R Bard, Inc.*, Exhibit 11 to Declaration of Richard Meyst Regarding Claim Construction; Civil Action No. 1:14-cv-03618; Judge John Z Lee; Filed Jul. 8, 2016.
*Medline Industries inc* vs*C.R. Bard. Inc.*. Declaration of Kevin A. Lake in Support of Medline Response to Bard Claim Construction Brief: Civil Action No. 1:14-cv-03618; Judge John Z. Lee; Filed Jul. 8, 2016.
*Medline Industries Inc* vs*C.R. Bard. Inc.*; Declaration of Barbara Weintraub Regarding Claim Construction; Civil Action No. 1:14-cv-03618; Judge John Z. Lee. Filed Jul. 8, 2016.
*Medline Industries Inc* vs*C.R. Bard. inc.*; Exhibit D to Declaration of Dylan J. Raife in Support of Bard Opening Claim Construction Brief. Civil Action No. 1:16-cv-03529; Judge Sharon Johnson Coleman; Filed Nov. 11, 2016.
*Medline Industries inc* vs*C.R. Bard. Inc.*; Exhibit 1 to Declaration of Richard Meyst Regarding Claim Construction; Civil Action No. 1:14-cv-03618; Judge John Z. Lee; Filed Jul. 8, 2016.
*Medline Industries Inc* vs*C.R. Bard. Inc*, Exhibit 4 to C.R. Bard's LPR 2 3 Contentions; Civil Action No. 1:17-cv-7216; Judge Sara L. Ellis; Filed Jan. 16, 2018.
*Medline Industries Inc* vs*C.R. Bard. Inc.*, Declaration of Peter Sauer in Support of Medline's Motion to Supplement Record; Civil Action No. 1:14-cv-03618; Judge John Z. Lee; Filed Mar. 23, 2017.
*Medline Industries Inc* vs*C.R. Bard. Inc.*; Exhibit D to Declaration of Kevin A. Lake; Civil Action No. 1:14-cv-03618. Judge John Z. Lee; Filed Jul. 8, 2016.
*Medline Industries Inc* vs*C.R. Bard. Inc.*, Exhibit 1 to Declaration of Brian Eutermoser in Support of Medline Surreply; Civil Action No. 1:14-cv-03618; Judge John Z. Lee; Filed Sep. 7, 2016.
*Medline Industries inc* vs *C R. Bard. Inc.*; Exhibit B to Declaration of Nicole M. Smith; Civil Action No. 1:14~cv43618; Judge John Z. Lee; Filed Jun. 4, 2016.
*Medline Industries Inc* vs *C R. Bard. inc.*; Exhibit D to Declaration of Nicole M Smith; Civil Action No. 1:14-cv-03618; Judge John Z. Lee; Filed Jun. 4, 2016.
*Medline Industries Inc* vs *C R. Bard. Inc.*; Exhibit E to Declaration of Nicole M. Smith; Civil Action No. 1:14-cv-03618: Judge John Z. Lee; Filed Jun. 4, 2016.
*Medline Industries Inc* vs *C R. Bard. Inc.*; Exhibit F to Declaration of Nicole M. Smith; Civil Action No. 1:14-cv-03618; Judge John Z. Lee; Filed Jun. 4, 2016.
*Medline Industries Inc* vs *C R. Bard. Inc*; C R. Bard's Opening Claim Construction Bnel; Civil Action No. 1:14-cv-03618; Judge John Z. Lee; Filed Jun. 4, 2016.
*Medline Industries Inc.* vs *C R. Bard. inc*; C.R Bard's Motion for Leave to Add Counterclaims; Civil Action No. 1:17-cv-7216; Judge Sara L. Ellis; Filed Feb. 27, 2018.
*Medline Industries Inc.* vs *C R. Bard. Inc*; Declaration of Dylan Raife in Support of Motion for Leave to Add CounterClaims; Civil Action No. 1:17-cv-7216; Judge Sara L. Eliis; Filed Feb. 27, 2018.
*Medline Industries Inc.* vs *C R. Bard. Inc*; Exhibit C to Declaration of Dylan Raife in Support of Motion for Leave to Add Counterclaims; Civil Action No. 1.17-cv-7216; Judge Sara L. Ellis; Filed Feb. 27, 2018.

*Medline industries Inc.* vs *C R. Bard. Inc*; Exhibit 1 to C R. Bard's LPR 2.3 Contentions, Civil Action No. 1:17-cv-7216, Judge Sara L. Ellis. Filed Jan. 16, 2018.
*Medline Industries Inc.* vs *C.R. Bard. Inc.*, Exhibit A to Declaration of Richard Meyst re Claim Construction: Civil Action No. 1:16-cv-03529: Judge Sharon Johnson Coleman; Filed Dec. 9, 2016.
*Medline Industries Inc.* vs *C.R Bard. Inc.*; Exhibit B to Declaration of Nicole Smith in Support of Bard Reply to Medline Claim Construction Brief; Civil Action No. 1.16-cv-03529; Judge Sharon Johnson Coleman; Filed Jan. 27, 2017.
*Medline Industries Inc.* vs *C.R. Bard. Inc.*; C R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit A—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit B—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit C—C. R. Bard's Final LPR 2.3 Contentions; Civil Action no. 1:17-cv-7216; Judge Sara L. Ellis; Filed Jul. 24, 2018.
*Medline Industries Inc.* vs *C.R. Bard, Inc.*; Exhibit C to Declaration of Nicole M. Smith; Civil Action No. 1:14-cv-03618; Judge John Z. Lee; Filed Jun. 4, 2016.
*Medline Industries Inc.* vs *C.R. Bard, Inc.*; Exhibit D—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit E—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit F—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit G—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit H—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard. Inc.*; Exhibit I—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard. Inc.*; Exhibit J—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard. Inc.*; Exhibit K—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard. Inc.*; Exhibit L—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit M—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard. Inc.*; Exhibit N—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard. Inc.*; Exhibit O—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard. Inc.*; Exhibit P—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit Q—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit R—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc.*; Exhibit S—C. R. Bard's Final LPR 2.3 Contentions; Civil Action No. 1:17-cv-7216; Judge Sara L. Ellis; Filed Jul. 24, 2018.

(56) References Cited

OTHER PUBLICATIONS

*Medline Industries Inc.* vs *C.R. Bard, Inc.*; Exhibit T—C. R. Bard's Final LPR 2.3 Contentions; Civil Action No. 1:17-cv-7216; Judge Sara L. Ellis; Filed Jul. 24, 2018.
*Medline Industries Inc.* vs *C.R. Bard, Inc*; C.R. Bard's LPR 3.1 Contentions; Civil Action No. 1:16-cs-3529; Judge Sharon Johnson Coleman; Filed Aug. 26, 2016.
*Medline Industries Inc.* vs *C.R. Bard, Inc*; Exhibit B to C R. Bard's LPR 2.3 Contentions; Civil Action No. 1:17-cv-7216; Judge Sara L. Ellis; Filed Jan. 16, 2018.
*Medline Industries* vs. *CR Bard, Inc*; No. 14-cv-3618; C.R. Bard's LPR 3.1 Contentions; Filed Nov. 24, 2015.
*Medline Industries Inc.* vs *C.R. Bard, Inc*; No. 1:14-cv-03618; Medline Industries Inc's Opposition to C.R.Bard Inc's Motion for Leave to File Second Amended Answer to Add Counterclaim; Filed Oct. 20, 2015.
*Medline Industries Inc.* vs *C.R. Bard, Inc*; No. 1:14-cv-03618; Medline Industries, Inc.'s Response to C.R. Bard's Initial Invalidity Contentions; Exhibits A-H; Dated Sep. 19, 2014.
*Medline Industries Inc.* vs *C.R. Bard, Inc*; No. 1:14-cv-03618; Notice of Medline Industries Inc's Motion to Dismiss C.R. Bard Inc's Inequitable Conduct Counterclaim and to strike affirmative defense for the '786 Patent; Filed Oct. 20, 2015.
*Medline Industries Inc.* vs *C.R. Bard, Inc*; No. 1:14-cv-03618; Response to Medline Industries, Inc.'s First Set of Interrogatories; Dated Sep. 26, 2014.
*Medline Industries Inc.* vs *C.R. Bard, Inc*; No. 1:14-cv-3618; Responses to Medline Industries, Inc.'s First set of Requests for the Production of Documents; Dated Sep. 26, 2014.
*Medline Industries Inc.* vs *C.R. Bard, Inc*; No. 1:17-cv-03618; Medline's Supplemental Responses to Bard's Interrogatory No. 1-24 (redacted), dated Apr. 20, 2016; Filed as IPR Peition Exhibit 2013 in IPR2019-00035 and IPR2019-00036.
*Medline Industries Inc.* vs *C.R. Bard, Inc*; No. 1:17-cv-3539; Medline's Second Supplemental Responses to Bard's Interrogatory No. 11, 14, and 15 (redacted), dated Oct. 26, 2017; Filed as IPR Peition Exhibit 2014 in IPR2019-00035 and IPR2019-00036.
*Medline Industries Inc.* vs *C.R. Bard, Inc*; No. 1:17-cv-7216; Medline's Objection and Response to Bard's First Set of Interrogatories (redacted), dated Oct. 1, 2018; Filed as IPR Peition Exhibit 2012 in IPR2019-00035 and IPR2019-00036.
*Medline Industries Inc.* vs *C.R. Bard, Inc*; No. 14-cv-3618; C.R. Bard's LPR 2.3 Contentions—Initial Non-Infringement; Exhibits 1 and A-H; Dated Sep. 5, 2014.
*Medline Industries Inc.* vs *C.R. Bard, Inc*: Transcript of Proceedings Claim Construction Hearing: Civil Action No. 1:14-cv-3618. Judge John Z. Lee; Dated Jan. 11, 2017.
Naming Characters on Cards website. URL:<https://web.archive.org/web/20060219171403/http://www.hubbardscupboard.org/brown_bear_brown_bear.html>. (2006) . . . Retrieved form Internet Dec. 11, 2013.
Notice of Allowance; EP Application No. 10251025.2-1501; Reference P112645EP00; dated Feb. 18, 2016.
Inter Partes Review—Patent Owner's Prelim. Response; U.S. Pat. No. 9,808,596; Inter Partes Review No. IPR2019-00223; Filed Mar. 7, 2019.
*Medline Industries Inc* vs *C.R Bard, Inc.*. Bard Opening Claim Construction Brief; Civil Action No. 1:16-cv-03529; Judge Sharon Johnson Coleman; Filed Nov. 17, 2017.
Webster's Dictionary Definition of "Intend"; Webster's Third New International Dictionary of the English Language unabridged (1961); filed as IPR Petition Exhibit 2016 in IPR 2019-00035.
"Appeal Decision", U.S. Appl. No. 12/785,064, filed May 21, 2010; dated May 18, 2016.
"Article 94(3) EPC Examination", European Application No. 10 251 025.2-1501; Reference P112645EP00; dated Mar. 13, 2015.
"Australian First Exam Report", AU Patent Application No. 2011351971; Patent Examination Report No. 1; dated Jul. 25, 2015.

"Bard IPR Exhibit", "Inter Partes Review Petition", IPR Exhibit—Carrow Declaration for U.S. Pat. No. 8,631,935; Susan Carrow Declaration; Mailed Dec. 30, 2014.
"Bard Medical Division Care & Catheterization Script", Care & Catheterization/Preventing UTI Script for education video; Preventing UTI: Care and Catheterization Techniques; Copyright 2006; AV0512-06 R12/05 XXX.
"Bard Publication", "A few important words about Catheter Care"; C.R. Bard, Inc; Copyright 2001 C.R. Bard, Inc.
"Bardex I.C. Complete Care StateLock Device 350 ml Urine Meter Foley Tray with Bacteriostatic Collection System", Bard Infection Control System; Bardex I.C. Complete Care Directions for Use; Copyright Dated Sep. 2006.
"Bardex I.C. Infection Control 350ml Urine Meter Foley Tray", Bard Infection Control System; Bardex I.C. Urine Meter Foley Tray Directions for Use; Copyright Dated 2006.
"Bardex I.C. Infection Control Foley Tray", Bard Infection Control System; Bardex I.C. Directions for Use Infection Control Foley Tray; Copyright Dated 2006.
"Decision Instituting Inter Partes Review", IPR2019-00035; U.S. Pat. No. 9,745,088; Mailed Apr. 10, 2019.
"Decision Instituting Inter Partes Review", IPR2019-00036; U.S. Pat. No. 9,745,088; Mailed Apr. 10, 2019.
"Decision Instituting IPR", IPR 2019-00208; U.S. Pat. No. 9,808,400; Dated Jun. 6, 2019.
"Decision Instituting Review", IPR 2019-00223; U.S. Pat. No. 9,808,596; Dated Jun. 6, 2019.
"EPO Intent to Grant", EPO Application No. 10251024.5; Filed Jun. 2, 2010; dated Nov. 2, 2012.
"Examiner's Answer", U.S. Appl. No. 13/153,265, filed Jun. 3, 2011; dated Dec. 17, 2013.
"Expert Report of Barbara Weintraub", Civil Action No. 1:14-cv-03618; Confidential Information Redacted Pursuant to Court Order; Dated Jun. 14, 2019.
"Expert Report of Barbara Weintraub", Civil Action No. 1:16-cv-03529; Confidential Information Redacted Pursuant to Court Order; Dated Aug. 1, 2019.
"Expert Report of Dr. Edward Yun", Civil Action No. 1:14-cv-03618; Confidential Information Redacted Pursuant to Court Order; Dated Jun. 13, 2019.
"Expert Report of Dr. Edward Yun", Civil Action No. 16-cv-3529; Confidential Information Redacted Pursuant to Court Order; Dated Aug. 1, 2019.
"Expert Report of Dr. Edward Yun Related to Damanges, Non-Infringement, and New Evidence of Alleged Secondary Considerations", Civil Action No. 1:14-cv-03618; Confidential Information Redacted Pursuant to Court Order; Dated Jul. 23, 2019.
"Expert Report of Dr. John Abraham", Civil Action No. 1:14-cv-03618; Confidential Information Redacted Pursuant to Court Order; Dated Jun. 14, 2019.
"Expert Report of Dr. John Abraham", Civil Action No. 1:16-cv-03529; Confidential Information Redacted Pursuant to Court Order; Dated Aug. 1, 2019.
"Expert Report of Dr. Steven Brooks", Civil Action No. 14-cv-3618; Confidential Information Redacted Pursuant to Court Order; Dated Jul. 25, 2019.
"Expert Report of Karl R Leingsing, MSME, PE Regarding Alleged Evidence of Secondary Considerations", Civil Action No. 1:14-cv-3618; Confidential Information Redacted Pursuant to Court Order; Dated Jun. 14, 2019.
"Expert Validity Report of Dr. John Abraham", Civil Action No. 1:14-cv-03618; Confidential Information Redacted Pursuant to Court Order; Dated Jul. 25, 2019.
"Extended EPO Exam Report", EPO App No. 10251025.2; Filed Jun. 2, 2010; dated Dec. 17, 2013.
"Final Written Decision", IPR 2019-00035; U.S. Pat. No. 9,745,008; Entered Apr. 8, 2020.
"Final Written Decision", IPR 2019-00036; U.S. Pat. No. 9,745,008; Entered Apr. 8, 2020.
"Final Written Decision", IPR 2019-00109; dated May 4, 2020; U.S. Pat. No. 9,795,761.
"Final Written Decision", IPR 2019-00208; U.S. Pat. No. 9,808,400; Entered Jun. 3, 2020.

(56) References Cited

OTHER PUBLICATIONS

"Final Written Decision", IPR 2019-00223; U.S. Pat. No. 9,808,596; Entered Jun. 3, 2020.
"Instructions", Naming a character website. URL: <https://web.archive.org/web/20080410122058/http://www.wilihow.com/Make-Your-Own-Anime-or-Mange-Character>. 2008.Retreived from Internet Dec. 10, 2013.
"Intent to Grant", Chinese Application No. 201180066491.4; Flled Dec. 30, 2011; dated Jul. 6, 2016.
"Intent to Grant", European Application No. 16177903.8-1501; Reference No. SJG/P112645EP02; dated Sep. 18, 2017.
"Inter Partes Review—Patent Owner Response", Inter Partes Review—Patent Owner Response; U.S. Pat. No. 8,631,935; Inter Partes Review No. IPR2015-00513; Filed Apr. 21, 2015.
"Inter Partes Review—Patent Owner Response", Inter Partes Review—Patent Owner Response; U.S. Pat. No. 8,448,786; IPR2015-00509; Filed Apr. 22, 2015.
"Inter Partes Review—Patent Owner Response", Inter Partes Review—Patent Owner Response; U.S. Pat. No. 8,631,935; Inter Partes Review No. IPR2015-00511; Filed Apr. 22, 2015.
"Inter Partes Review—Patent Owner Response", Inter Partes Review—Patent Owner Response; U.S. Pat. No. 8,678,190; Inter Partes Review No. IPR2015-00514; Filed Apr. 21, 2015.
"Inter Partes Review—Patent Owner's Prelim Response", U.S. Pat. No. 9,745,088; Inter Partes Review No. IPR2019-00035; Filed Jan. 11, 2019.
"Inter Partes Review—Patent Owner's Prlim Response", U.S. Pat. No. 9,745,088; Inter Partes Review No. IPR2019-00036; Filed Jan. 11, 2019.
Inter Partes Review No. IPR2019-00109, Petition for Review; U.S. Pat. No. 9,795,761; Filed Oct. 24, 2018.
"Inter Partes Review Petition", Exhibit—Amendment filed on Apr. 3, 2013 for U.S. Appl. No. 12/495,148, filed Jun. 30, 2009.
"Inter Partes Review Petition", Exhibit—Bard DFU; Bardex Infection Control Foley Tray; Copyright 2006, publication date unknown.
"Inter Partes Review Petition", Exhibit—Bardex DFU; Directions for Use/Patient Education Information—Urology; Unknown Publication Date.
"Inter Partes REview—Patent Owner REsponse Inter Partes Review Petition", Exhibit—Declaration of Susan Carrow for U.S. Pat. No. 8,631,935 claims 1-4 and 11-20; Mailed Dec. 30, 2014.
"Inter Partes REview—Patent Owner REsponse Inter Partes Review Petition", Exhibit—Dorland's Definition of Bag; Dorland's Illustrated Medical Dictionary; 31st Edition; Publication Date Unknown.
"Inter Partes Review Petition", Exhibit—EC Guideline 1998; "A Guideline on the Readability of the Label and Package Leaflet of Medicinal Products for Human Use"; Published Sep. 29, 1998 (Sep. 29, 1998); Mailed Dec. 30, 2014.
Inter Partes Review Petition, Exhibit—Encyclopedia Dictionary of Medicine, Nursing and Allied Health; Miller Keane, Seventh Edition.
Inter Partes Review Petition, Exhibit—FAQs "Catheter-Associated Urinary Tract Infection"; Unknown Publisher; Unknown Publication Date.
"Inter Partes Review Petition", Exhibit—FDA Article; Guidance for the Content of Premarkt Notifications fro Conventional and Antimicrobial Foley Catheters; http://www.fda.gov/medicaldevices/deviceregulationandguidance/guidancedocuments/ucm080884.htm; Unknown Publication Date.
"Inter Partes Review Petition", Exhibit—Health Protection Scotland; CAUTI Maintenance Bundel; Version 2, Feb. 2008.
"Inter Partes Review Petition", Exhibit—Infection Control Today Article; Medical Center Cuts Catheterizations by 21 Percent with Foley Catheter Management System; Published 2010.
"Inter Partes Review Petition", Exhibit—Kimmel Declaration for U.S. Pat. No. 8,631,935 claims 1-4 and 11-20; Declaration of Dr. Robert M. Kimmel; Mailed Dec. 30, 2014.
"Inter Partes Review Petition", Exhibit—Medical News Today Article; 'Getting to Zero:' Medlines' Erase Cauti Program Helps Hospitals Reduce Catheter Use by 20 Percent; Article Date Apr. 13, 2011.
"Inter Partes Review Petition", Exhibit—Medline Initial Infringement Contentions; *Medline Industries* vs. *C.R. Bard*; Dated Aug. 22, 2014.
"Inter Partes Review Petition", Exhibit—Morning Start Article; "Floyd Medical Center Reduces Catheter-Associated Urinary Tract Infections 83 Percent and Catheter Use by 23 Percent"; Published Jan. 2011.
"Inter Partes Review Petition", Exhibit—Mosby's Pocket Guide Excerpt; Mosby's Pocket Guide to Basic Skills and Procedures; Sixth Edition; Perry & Potter; "Urinary Catheter: Indwelling, Straight, Care and Removal"; Unknown Publication Date.
"Inter Partes Review Petition", Exhibit—Nursing Standard; Article in Learning Zone—Continue Professional Development; "Reducing the risks associated with urinary catheters"; Published Mar. 25, 2009.
"Inter Partes Review Petition", Exhibit—RCE Filed Nov. May 31, 2011 for U.S. Appl. No. 12/495,148, filed Jun. 30, 2009.
"Inter Partes Review Petition", Exhibit—Response to Office Action in U.S. Appl. No. 12/495,148, filed Jun. 30, 2009; Response Filed Nov. 19, 2010.
"Inter Partes Review Petition", Exhibit—Soroka Glossary 'Bag'; Illustrated Glossary of Packaging Terminology, second edition; Walter Soroka; publication unknown.
"Inter Partes Review Petition", Exhibit—Soroka Glossary_wrap; Illustrated Glossary of Packaging Terminology; second edition; publication date unknown.
"Inter Partes Review Petition", Exhibit—The Journal of Healthcare Contracting, Oct. 2012; "Catheter-associated urinary tract infections".
"Inter Partes Review Petition", Exhibit—Websters Dictionary Definition of Dispose; Webster's Third New International Dictionary; Copyright 2003; publication date unknown.
"Inter Partes Review Petition", Exhibit; Carrow CV—Susan Carrow CV; Mailed Dec. 30, 2014.
"Inter Partes Review Petition", Exhibit; EC Guideline 2009; "Guideline on the Readability of the Labelling and Package Leaflet of Medicinal Products for Human Use"; Revision 1 Published Jan. 12, 2009 (Jan. 12, 2009); Mailed Dec. 30, 2014.
"Inter Partes Review Petition", Exhibit; Kimmel CV—Dr. Robert M. Kimmel; Mailed Dec. 30, 2014.
"Inter Partes Review Petition", IPR Exhibit—Carrow Declaration for U.S. Pat. No. 8,631,935 claims 1-4 and 11-20; Susan Carrow Declaration; Mailed Dec. 30, 2014.
"Inter Partes Review Petition", IPR Exhibit—Carrow Declaration for U.S. Pat. No. 8,768,190; Declaration of Susan Carrow; Mailed Dec. 30, 2014.
"Inter Partes Review Petition", IPR Exhibit—Kimmel Declaration U.S. Pat. No. 8,448,786 Patent; Dr. Robert M. Kimmel Declaration.
"Inter Partes Review Petition", IPR Exhibit—Kimmel Declaration for U.S. Pat. No. 8,631,935 claims 1-4 and 11-20; Declaration of Dr. Robert M. Kimmel; Mailed Dec. 30, 2014.
"Inter Partes Review Petition", IPR Exhibit—Kimmel Declaration for U.S. Pat. No. 8,631,935 claims 7-8, 10, 21-23, 25, 27-28, and 30-34; Declaration of Dr. Robert M. Kimmel; Mailed Dec. 30, 2014.
"Inter Partes Review Petition", IPR Exhibit—Kimmel Declaration for U.S. Pat. No. 8,768,190; Declaration of Dr. Robert M. Kimmel; Mailed Dec. 30, 2014.
"Inter Partes Review Petition", IPR Exhibit—Susan Carrow Declaration U.S. Pat. No. 8,448,786 patent; mailed Dec. 30, 2014.
"Inter Partes Review Petition for 8,448,786", U.S. Pat. No. 8,448,786; Filed Dec. 30, 2014; Mailed Dec. 30, 2014.
"Inter Partes Review Petition for U.S. Pat. No. 8,631,935", Inter Partes Review Petition for U.S. Pat. No. 8,631,935 for claims 1-4 and 11-20; Filed Dec. 30, 2014.
"Inter Partes Review Petition for U.S. Pat. No. 8,631,935", Inter Partes Review Petition for U.S. Pat. No. 8,631,935 for Claims 7-8, 10, 21-23, 25, 27-28, and 30-34; Filed Dec. 30, 2014.

(56) References Cited

OTHER PUBLICATIONS

"Inter Partes Review Petition for U.S. Pat. No. 8,678,190", Inter Partes Review Petition for U.S. Pat. No. 8,678,190; Filed Dec. 30, 2014.
"Inter Partes Review Petition for U.S. Pat. No. 9,745,088", IPR-0036; Filed Oct. 4, 2018.
"Inter Partes Review Petition for U.S. Pat. No. 9,745,088", IPR2019-0035, filed Oct. 4, 2018.
"IPR 2015-00514—Patent Owner's Objection to Evidence", IPR 2015-00514—Patent Owner's Objection to Evidence Submitted During a Preliminary Proceeding; U.S. Pat. No. 8,678,190; Mailed Jul. 13, 2015.
"IPR 2015-00514—Patent Owner's Request for Adverse Judgement", U.S. Pat. No. 8,678,190; Mailed Jul. 23, 2015.
"IPR 2015-00514—Request for Rehearing Denied", IPR2015-00514; U.S. Pat. No. 8,678,190; Decision on Request for Rehearing—Denied; Mailed Jul. 16, 2015.
"IPR 2015-00514 Petitioner's Request for Rehearing", IPR 2015-00514 Petitioner's Request for Rehearing; U.S. Pat. No. 8,678,190; Dated Jul. 10, 2015.
"IPR 2019-00109", Exhibit 1031—Declaration of Jennifer Tomes filed in U.S. Appl. No. 12/647,515 dated Dec. 7, 2012.
"IPR 2019-00109", U.S. Pat. No. 9,795,761; Filed Oct. 24, 2018; Declaration of Dr. Edward Yun.
"IPR Decision Instituting Inter Partes Review", IPR2019-00109; U.S. Pat. No. 9,795,761; Mailed May 6 2019.
"IPR Exhibit 1002", Declaration of Pliska; IPR2019-0035, Filed Oct. 4, 2018.
"IPR Exhibit 1003", Declaration of Yun; IPR2019-0035; Filed Oct. 4, 2018.
"IPR Exhibit 1022", Email from Medline counsel re claims constructions; IPR2019-0035; Filed Oct. 4, 2018.
"IPR Petition Exhibit 1016", Excerpt from "The Design of Everyday Things"; IPR2019-0035; Filed Oct. 4, 2018.
"IPR Petition Exhibit 1024", Email from Bard counsel re claims constructions; IPR2019-0035; Filed Oct. 4, 2018.
"IPR0215-00513 Scheduling Order", U.S. Pat. No. 8,631,935; Mailed Jul. 15, 2015.
"IPR2015-00509 Institution Decision", IPR2015-00509; U.S. Pat. No. 8,448,786; Mailed Jul. 15, 2015; Decision Denying Institution of Inter Partes Review.
"IPR2015-00511 Institution Decision", IPR2015-00511; U.S. Pat. No. 8,631,935; Entered Jul. 15, 2015; Decision Denying Institution of Inter Partes Review.
"IPR2015-00513—Request for Adverse Judgement", IPR2015-00513—Request for Adverse Judgement; Granted—Proceedings Terminated; U.S. Pat. No. 8,631,935; Entered Aug. 11, 2015.
IPR2015-00513—Patent Owner's Request for Adverse Judgement, U.S. Pat. No. 8,631,935; Mailed Jul. 23, 2015.
"IPR2015-00513 Institution Decision", IPR2015-00513 Institution Decision; U.S. Pat. No. 8,631,935; Entered Jul. 15, 2015; Decision Institution of Inter Partes Review.
"IPR2015-00514—Scheduling Order", U.S. Pat. No. 8,678,190; Mailed Jun. 26, 2015.
"IPR2015-00514 Decision Institution of Inter Partes Review", IPR2015-00514; U.S. Pat. No. 8,678,190; Mailed Jun. 26, 2015; Decision Institution of Inter Partes Review.
"IPR2015-00514 Judgement—Termination of Proceeding", U.S. Pat. No. 8,678,190; Mailed Jul. 24, 2015.
"IPR2019-00109", Exhibit 1026—Bard's Opening Claim Construction Brief; Civil Action No. 1:17-cv-07216; Dated Oct. 10, 2018; Filed Oct. 24, 2018 as exhibit 1026.
"IPR2019-00109", Exhibit 1030—Medline Industries, Inc.'s Final Infringement Contentions; Filed Jul. 24, 2018 in Civil Action No. 1:17-cv-07216; Filed as exhibit Oct. 24, 2018.
"IPR2019-00109", U.S. Pat. No. 9,795,761; Filed Oct. 24, 2018; Exhibit 1002 Declaration of Michael Plishka.
"Markman Decision", *Medline Industries, Inc.* vs *C.R. Bard, Inc*; Case No. 1:16-cv-03529\; Memorandum Opinion and Order; Judge Sharon Johnson Coleman Issued Dec. 28, 2018.
"Markman Hearing", *Medline Industries, Inc.* vs *C.R. Bard, Inc*; Case No. 1:17-cv-07216; Memorandum Opinion and Order; Judge Sara L. Ellis; Issued Jan. 28, 2019.
"Medline Catalog", Argyle Trocar Catheter Kits by Covidien; http://www.medline.com/sku/item/MDPSWD565028; Unknown Publication Date but believed to be prior to filing of present application.
"Medline Catalog", Argyle Turkel Safety Thoracentesis System by Covidien; 6"; http://www.medline.com/sku/item/MDPKDL5016; Unknown Publication Date but believed to be prior to filing of present application.
"Medline Catalog", Argyle Turkel Safety Thoracentesis System by Covidien; http://www.medline.com/sku/item/MDPKDL5014; Unknown Publication Date but believe to be prior to filing of present application.
"Medline Catalog", Paracentesis Trays by Covidien; http://www.medline.com/sku/item/MDPSWD568006; Unknown Publication Date but believed to be prior to filing of present application.
"Medline Catalog", Paracentesis Trays by Halyard Health; http://www.medline.com/sku/item/MDPBAA61450; Unknown Publication Date but believed to be prior to filing of present application.
"Medline Catalog", Safe-T Thoracentesis/Paracentesis Tray by Carefusion; http://www.medline.com/sku/item/MDPBXTTPT1000SP; Unknown publication date but believed to be prior to filing of present application.
"Medline Catalog", Thoracentesis Trays by Carefusion; http://www.medline.com/sku/item/MDPBXTPIG1280K; Unknown publication date but believed to be prior to filing of present application.
"Medline Catalog", Turkel Safety Thoracentesis Procedure Trays by Covidien; 5"; http://www.medline.com/sku/item/MDPKDL566075; Unknown Publication date but believed to be prior to present application filing date.
"Medline Catalog", Turkel Safety Thoracentesis Procedure Trays by Covidien; http://www.medline.com/jump/sku/x/MDPKDL566059; Unknown Publication date but believed to be prior to present application filing date.
"NonFinal Office Action", U.S. Appl. No. 13/680,902, filed Apr. 11, 2014; dated Dec. 2, 2014.
"Notice of Acceptance", Australian Application No. 2011351971; Filed Dec. 30, 2011; dated May 13, 2016.
"Notice of Allowance", Canadian Application No. 2,705,647; Filed May 27, 2010; dated Oct. 12, 2017.
"Notice of Allowance", Candaian Application No. 2,705,670; dated Nov. 3, 2017.
"Notice of Allowance", Chinese Application No. 201280035240.4; dated Nov. 7, 2017.
"Office Action", Australian Application No. 2011351971; Reference No. 35204298/GP; dated Feb. 18, 2016.
"Office Action", Chinese Application No. 201180066491.4; dated Mar. 24, 2015.
"Office Action", Chinese Application No. 201180066491.4; dated Nov. 11, 2015.
"Office Action", Chinese Application No. 201280035246.1; Filed May 11, 2012; dated Jul. 15, 2016.
"Office Action", Chinese Application No. 201280035246.1; Filed May 11, 2012; dated Nov. 28, 2016.
"Office Action Received", Chinese App No. 201280035246.1; NonFinal OA; dated Sep. 16, 2015.
"Opening Expert Report of Karl R Leinsing, MSME, PE", Civil Action No. 1:14-cv-3618; Confidential Information Redacted Pursuant to Court Order; Dated Jun. 14, 2019.
"Opening Expert Report of Karl R. Leinsing, MSME, PE", Civil Action No. 1:16-cv-3529; Confidential Information Redacted Pursuant to Court Order; Dated Aug. 1, 2019.
"Petition for Inter Partes Review", IPR 2019-00208; U.S. Pat. No. 9,808,400; Filed Nov. 7, 2018.
"Petition for Inter Partes Review", IPR 2019-00223; U.S. Pat. No. 9,808,596; Filed Nov. 7, 2018.
"Publication", European Commission: Pharmaceutical Committee "A Guideline on the Readability of the Label and Package Leaflet of Medicinal Products for Human Use"; Dated Sep. 29, 1998.
"Rebuttal Expert Report of Barbara Weintraub", Civil Action No. 1:14-cv-03618; Confidential Information Redacted Pursuant to Court Order; Dated Jul. 25, 2019.

(56) References Cited

OTHER PUBLICATIONS

"Rebuttal Expert Report of Richard Hillstead, Ph.D.", Civil Action No. 1:14-cv-3618; Confidential Information Redacted Pursuant to Court Order; Dated Jun. 14, 2019.
"Second Office Action", Chinese Application No. 201280035240.4; dated Jun. 23, 2016.
"Third Office Action", Chinese Application No. 201280035240.4; dated Apr. 1, 2017.
"YouTube Training Video", https://www.youtube.com/watch?v=YwqcRUP35nl&list=UUG7a6tFPh1wvF0QDMZ3DarQ, ; Unknown publication date but believed to be prior to filing of present application.
"YouTube Training Video", https://www.youtube.com/watch?v=ISBya_5cIM, ; Unknown publication date but believed to be prior to filing of present application.
"Byun, Sung C. PCT Search Report", PCT/US2011/068193; Filed Dec. 30, 2011; dated Aug. 22, 2012.
"Byun, Sung C. PCT Search Report", PCT/US2012/039311; Filed May 24, 2011; dated Oct. 25, 2012.
"Byun, Sung Cheal PCT Search Report and Written Opinion", PCT/US2012/037524; Filed May 11, 2012; dated Nov. 16, 2012.
"Cavanna, Mark Ex Parte Quayle Action", U.S. Appl. No. 29/380,474, filed Dec. 6, 2010; Mailed Aug. 14, 2012.
"Cavanna, Mark Final OA", U.S. Appl. No. 29/479,600, filed Jan. 17, 2014; Mailed Jun. 1, 2017.
"Cavanna, Mark NonFinal OA", U.S. Appl. No. 29/479,600, filed Jan. 17, 2014; Mailed Jan. 3, 2018.
"Cavanna, Mark NonFinal Office Action", U.S. Appl. No. 29/380,474, filed Dec. 26, 2012; dated Mar. 27, 2012.
"Cavanna, Mark Non-Final Office Action", U.S. Appl. No. 29/479,600, filed Jan. 17, 2014; dated Sep. 26, 2016.
"Cavanna, Mark Notice of Allowance", U.S. Appl. No. 29/338,022, filed Jun. 3, 2009; dated Oct. 1, 2009.
"Cavanna, Mark Notice of Allowance", U.S. Appl. No. 29/362,279, filed May 2010, dated Sep. 19, 2011.
"Cavanna, Mark Notice of Allowance", U.S. Appl. No. 29/444,526, filed Jan. 31, 2013; dated Oct. 17, 2013.
European Patent Office, Extended EPO Search Report, Application No. 10251024.5, in the Name of Medline Industries, dated Oct. 18, 2010.
"European Patent Office, Extended EPO Search Report", EPO Application No. 10251025.2, in the Name of Medline Industries, dated Sep. 29, 2010.
"Examiner, Chinese Patent Office First Office Action", CN Application No. 201020219785.9; dated Nov. 18, 2010; Filed Jun. 3, 2010.
"Gilligan, C. Luke Notice of Allowance", U.S. Appl. No. 13/153,265, filed Jun. 3, 2011; dated Jun. 15, 2017.
"Gimenez Burgos, R European Examination Report", European Application No. 11 854 003.8-1659; Ref SJG/P128064EP00; dated Jan. 22, 2015.
"Gimenez Burgos, R Extended European Search Report", 11854003.8; Filed Dec. 30, 2011; dated Jun. 3, 2014.
"Gimenez Burgos, R Extended European Search Report", EPO App No. 12 79 3939; Reference No. SJG/P130269EP00; dated Jan. 27, 2015.
"Gimenez Burgos, R Extended European Search Report", EU App No. 12792423.1-1659/2713933; PCT/US2012039311; REference No. SJG/P130270EP00; dated Jan. 27, 2015.
"Hand, Melanie J. Final OA", U.S. Appl. No. 12/785,064, filed May 21, 2010; Mailed Jun. 5, 2013.
"Hand, Melanie J. NonFinal OA", U.S. Appl. No. 12/785,064, filed May 21, 2010; Mailed Feb. 1, 2013.
"Hand, Melanie J. NonFinal OA", U.S. Appl. No. 13/115,053, filed Jun. 7, 2011; Mailed May 9, 2013.
"Hand, Melanie J. NonFinal OA", U.S. Appl. No. 13/155,026, filed Jun. 7, 2011; Mailed Nov. 30, 2012.
"Hand, Melanie J. NonFinal OA", U.S. Appl. No. 13/860,902, filed Apr. 11, 2013; Mailed Apr. 1, 2016.
"Hand, Melanie J. NonFinal OA", U.S. Appl. No. 14/165,044, filed Jan. 27, 2014; Mailed Oct. 26, 2015.
"Hand, Melanie J. Notice of Allowance", U.S. Appl. No. 13/155,026, filed Jun. 7, 2011; dated Feb. 1, 2013.
"Hand, Melanie J. Notice of Allowance", U.S. Appl. No. 13/155,054, filed Jun. 7, 2011; dated Oct. 28, 2013.
"Hand, Melanie J. Notice of Allowance", U.S. Appl. No. 13/860,902, filed Apr. 11, 2013; dated Aug. 4, 2015.
"Hand, Melanie Jo Appeal Decision", U.S. Appl. No. 12/785,064, filed May 21, 2010; dated May 18, 2016.
"Hand, Melanie Jo Final OA", U.S. Appl. No. 13/860,902, filed Apr. 11, 2013; Mailed May 22, 2015.
"Klein, Benjamin J. NonFinal OA", U.S. Appl. No. 15/5051,964, filed Feb. 24, 2016; Mailed Jan. 7, 2019.
"Klein, Benjamin Jacob Notice of Allowance", U.S. Appl. No. 15/051,964, filed Feb. 24, 2016; dated Aug. 21, 2019.
"Lawrence, Samantha Notice of Allowance", U.S. Appl. No. 29/479,600, filed Jan. 17, 2014; dated Feb. 24, 2020.
"Lawrence, Samantha Q. Notice of Allowance", U.S. Appl. No. 29/479,600, filed Jan. 17, 2014; dated Apr. 25, 2019.
"Long, Fonya M Appeal Decision", U.S. Appl. No. 13/154,265, filed Jun. 3, 2011; Mailed Oct. 6, 2016.
"Mackenzie, Kristian Office Action", Canadian Application No. 2,705,647; dated Feb. 10, 2017.
"Mackenzie, Kristian Office Action", Canadian Application No. 2,705,647; dated Apr. 21, 2016.
"Mackenzie, Kristian Office Action", Canadian Application No. 2,705,670; dated Feb. 10, 2017.
"Mackenzie, Kristian Office Action", Canadian Application No. 2,705,670; Ref. No. 15468-8; dated Apr. 25, 2016.
"Marcetich, Adam Non-Final OA", U.S. Appl. No. 15/640,224, filed Jun. 30, 2017; Mailed Jul. 10, 2019.
"Marcetich, Adam NonFinal Office Action", U.S. Appl. No. 15/684,787, filed Aug. 23, 2017; dated Nov. 4, 2019.
"Marcetich, Adam Notice of Allowance", U.S. Appl. No. 13/860,902, filed Apr. 11, 2013; dated Nov. 8, 2016.
"Marcetich, Adam Notice of Allowance", U.S. Appl. No. 13/860,902, filed Apr. 11, 2013; dated Sep. 14, 2016.
"Marcetich, Adam Notice of Allowance", U.S. Appl. No. 14/165,044, filed Jan. 27, 2014; dated Feb. 28, 2017.
"Marcetich, Adam Notice of Allowance", U.S. Appl. No. 14/793,455, filed Jul. 7, 2015; dated Jul. 20, 2017.
"Marcetich, Adam Notice of Allowance", U.S. Appl. No. 15/684,787, filed Aug. 23, 2017; dated Feb. 27, 2020.
"Marcetich, Adam M. Final OA", U.S. Appl. No. 14/165,044, filed Jan. 27, 2014; Mailed Aug. 11, 2016.
"Marcetich, Adam M. Notice of Allowance", U.S. Appl. No. 15/640,224, filed Jun. 30, 2017; dated Nov. 21, 2019.
"Marcitech, Adam NonFinal OA", U.S. Appl. No. 14/793,455, filed Jul. 7, 2015; Mailed May 3, 2017.
"Medline, Medline Aritcle/Brochure", Published 2008.
Mian, Ali Canadian Application No. 2837324; Mailed Oct. 6, 2020.
"Mian, Ali Non-Final Office Action", Canadian Application No. 2,837,324; dated Oct. 3, 2018.
"Mian, Ali Office Action", Canadian Application No. 2,837,324; dated Sep. 3, 2019.
Ortega, Rafael et al., "Female Urethral Catheterization", N. Engl. J. Med vol. 358:e15; published 2008.
"Pass, Natalie Final OA", U.S. Appl. No. 13/153,265, filed Jun. 3, 2011; Mailed Jul. 12, 2013.
"Pass, Natalie NonFinal OA", U.S. Appl. No. 13/153,265, filed Jun. 3, 2011; Mailed Mar. 5, 2013.
"Poon, Robert Appeal Decision", U.S. Appl. No. 12/647,515, filed Dec. 27, 2009; Mailed Jan. 19, 2018.
"Poon, Robert Appeal Decision", U.S. Appl. No. 13/153,300, filed Jun. 3, 2011; Mailed Oct. 12, 2016.
"Poon, Robert Appeal Decision", U.S. Appl. No. 13/374,509, filed Dec. 30, 2011; Mailed Oct. 24, 2016.
"Poon, Robert Appeal Decision", U.S. Appl. No. 14/265,920, filed Apr. 30, 2014; Mailed Aug. 1, 2018.
"Poon, Robert Final OA", U.S. Appl. No. 12/647,515, filed Dec. 27, 2009; Mailed Apr. 7, 2015.

(56) References Cited

OTHER PUBLICATIONS

"Poon, Robert Final OA", U.S. Appl. No. 12/647,515, filed Dec. 27, 2009; Mailed May 13, 2013.
"Poon, Robert Final OA", U.S. Appl. No. 12/846,675, filed Jul. 29, 2010; Mailed Dec. 18, 2013.
"Poon, Robert Final OA", U.S. Appl. No. 13/153,300, filed Jun. 3, 2011; Mailed Aug. 6, 2013.
"Poon, Robert Final OA", U.S. Appl. No. 13/374,509, filed Dec. 30, 2011; Mailed Aug. 6, 2013.
"Poon, Robert Final OA", U.S. Appl. No. 14/265,909, filed Apr. 30, 2014; Mailed Jan. 10, 2017.
"Poon, Robert Final OA", U.S. Appl. No. 14/265,909, filed Apr. 30, 2015; Mailed Oct. 5, 2015.
"Poon, Robert Final OA", U.S. Appl. No. 14/265,920, filed Apr. 30, 2014; Mailed Oct. 2, 2015.
"Poon, Robert Final OA", U.S. Appl. No. 14/718,792, filed May 21, 2015; Mailed Jan. 5, 2016.
"Poon, Robert Final OA", U.S. Appl. No. 15/067,903, filed Mar. 11, 2016; Mailed Jan. 13, 2017.
"Poon, Robert Final Office Action", U.S. Appl. No. 12/495,148, filed Jun. 30, 2009, dated Mar. 3, 2011.
"Poon, Robert Final Office Action", U.S. Appl. No. 12/495,148, filed Jun. 30, 2009; dated Jul. 31, 2013.
"Poon, Robert Final Office Action", U.S. Appl. No. 12/846,675, filed Jul. 29, 2010; dated Sep. 26, 2012.
"Poon, Robert Final Office Action", U.S. Appl. No. 14/718,912, filed May 21, 2015; dated Jan. 5, 2016.
"Poon, Robert Final Office Action", U.S. Appl. No. 15/703,514, filed Sep. 13, 2017; dated May 2, 2019.
"Poon, Robert Final Office Action", U.S. Appl. No. 15/703,514; dated May 2, 2019.
"Poon, Robert Final Office Action", U.S. Appl. No. 15/803,383, filed Nov. 3, 2017; dated Jul. 25, 2019.
"Poon, Robert Final Office Action", U.S. Appl. No. 15/804,520, filed Nov. 6, 2017; dated Aug. 8, 2019.
"Poon, Robert Final Office Action", U.S. Appl. No. 16/258,231, filed Jan. 25, 2019; dated Jul. 15, 2020.
"Poon, Robert NonFinal OA", U.S. Appl. No. 12/495,148, filed Jun. 30, 2009; Mailed Oct. 4, 2012.
"Poon, Robert NonFinal OA", U.S. Appl. No. 12/647,515, filed Dec. 27, 2009; Mailed Dec. 18, 2013.
"Poon, Robert NonFinal OA", U.S. Appl. No. 12/846,675, filed Jul. 29, 2010; Mailed Sep. 10, 2013.
"Poon, Robert NonFinal OA", U.S. Appl. No. 14/265,909, filed Apr. 30, 2014; Mailed Sep. 12, 2016.
"Poon, Robert NonFinal OA", U.S. Appl. No. 14/265,909, filed Apr. 30, 2014; Mailed Dec. 31, 2014.
"Poon, Robert NonFinal OA", U.S. Appl. No. 14/265,920, filed Apr. 30, 2014; Mailed Dec. 30, 2014.
"Poon, Robert NonFinal OA", U.S. Appl. No. 14/718,792, filed May 21, 2015; Mailed Nov. 19, 2015.
"Poon, Robert NonFinal OA", U.S. Appl. No. 15/067,903, filed Mar. 11, 2016; Mailed Jun. 30, 2016.
"Poon, Robert NonFlnal OA", U.S. Appl. No. 15/803,383, filed Nov. 3, 2017; Mailed Mar. 7, 2018.
"Poon, Robert NonFinal OA", U.S. Appl. No. 15/804,520, filed Nov. 6, 2017; Mailed Jan. 19, 2018.
"Poon, Robert Non-Final OA", U.S. Appl. No. 14/265,909, filed Apr. 30, 2014; Mailed Aug. 24, 2017.
"Poon, Robert NonFinal Office Action", U.S. Appl. No. 15/703,514, filed Sep. 13, 2017; dated Jun. 22, 2018.
"Poon, Robert NonFinal Office Action", U.S. Appl. No. 12/647,515, filed Dec. 27, 2009; dated Jun. 28, 2012.
"Poon, Robert NonFinal Office Action", U.S. Appl. No. 12/846,675, filed Jul. 29, 2010; dated Dec. 22, 2011.
"Poon, Robert NonFinal Office Action", U.S. Appl. No. 13/153,300, filed Jun. 3, 2011; dated Oct. 1, 2012.
"Poon, Robert NonFinal Office Action", U.S. Appl. No. 13/374,509, filed Dec. 30, 2011; dated Oct. 2, 2012.
"Poon, Robert NonFinal Office Action", U.S. Appl. No. 15/703,514, filed Sep. 13, 2017; dated Mar. 17, 2020.
"Poon, Robert NonFinal Office Action", U.S. Appl. No. 15/804,520, filed Nov. 6, 2017; dated Jun. 6, 2018.
"Poon, Robert NonFinal Office Action", U.S. Appl. No. 16/258,231, filed Jan. 25, 2019; dated Oct. 2, 2019.
"Poon, Robert Non-Final Office Action", U.S. Appl. No. 12/495,148, filed Jun. 30, 2009; first inventor: Jennifer E. Tomes; dated Aug. 4, 2010.
"Poon, Robert Non-Final Office Action", U.S. Appl. No. 15/803,383, filed Nov. 3, 2017; dated Mar. 16, 2020.
"Poon, Robert Non-Final Office Action", U.S. Appl. No. 15/803,393, filed Nov. 3, 2017; dated Oct. 15, 2018.
"Poon, Robert Non-Final Office Action", U.S. Appl. No. 15/804,520, filed Nov. 6, 2017; dated Nov. 2, 2018.
"Poon, Robert Notice of Allowance", U.S. Appl. No. 12/495,148, filed Jun. 30, 2009; dated Nov. 20, 2013.
"Poon, Robert Notice of Allowance", U.S. Appl. No. 12/846,675, filed Jul. 29, 2010; dated Apr. 30, 2014.
"Poon, Robert Notice of Allowance", U.S. Appl. No. 14/265,920, filed Apr. 30, 2014; dated Nov. 28, 2018.
"Poon, Robert Notice of Allowance", U.S. Appl. No. 14/718,792, filed May 21, 2015; dated Feb. 2, 2016.
"Poon, Robert Notice of Allowance", U.S. Appl. No. 14265,909, filed Apr. 30, 2014; dated Oct. 2, 2017.
"Poon, Robert Notice of allowance", U.S. Appl. No. 15/067,903, filed Mar. 11, 2016; dated Aug. 23, 2017.
"Poon, Robert Notice of Allowance", U.S. Appl. No. 15/703,514, filed Sep. 13, 2017; dated Nov. 23, 2020.
"Poon, Robert Notice of Allowance", U.S. Appl. No. 15/803,383, filed Nov. 3, 2017; dated Nov. 27, 2020.
"Poon, Robert Restriction Requirement", U.S. Appl. No. 12/647,515, filed Dec. 27, 2009; dated May 23, 2012.
"Pothier, Andrew NonFinal OA", Canadian Application No. 2,837,289; Mailed Feb. 14, 2018.
"Pothier, Andrew NonFinal Office Action", Canadian Patent Application No. 2,822,905; dated Aug. 31, 2018.
"Pothier, Andrew Non-Final Office Action", Canadian Application No. 2,837,289; dated Jun. 27, 2019.
"Pothier, Andrew Non-Final Office Action", Canadian Application No. 2,822,905; File No. 15468-P44352CA00; dated Dec. 18, 2017.
"Pothier, Andrew Office Action", Canadian Application No. 2,822,905; dated Jun. 13, 2019.
"Pothier, Andrew Office Action", Canadian Application No. 2,822,905; dated May 1, 2017.
"Pothier, Andrew Office Action", Canadian Application No. 2,837,289; dated Oct. 29, 2018.
"Pothier, Andrew Office Action", Canadian Application No. 2,837,289; dated Feb. 27, 2020.
"Pothier, Andrew Office Action", Canadian Application No. 2,837,289; dated Oct. 14, 2020.
"Pothier, Andrew Office Action", Canadian Application No. 2822905; dated Feb. 27, 2020.
"Power, Postoperative behaviour changes and pain in children, 2 to 12 years, following inpatient and day case surgery", University College London; http://discovery.ucl.ac.uk/643438/1/643438.pdf, Aug. 2010.
"Prange, Sharon M. Response to First Office Action", U.S. Appl. No. 12/004,796, filed Dec. 21, 2007; dated Oct. 28, 2009.
"Schultz, Ottmar Extended European Search Report", EP Application No. 16177903.8-1501; Filed Jun. 30, 2009; dated Oct. 27, 2016.
"Thomsen, Todd Male Urethral Catheterization", N. Engl. J. Med vol. 354:e22; Published 2006.
"Van Poelgeest, A Exam Report", EP Application No. 12792423.1; dated Sep. 17, 2019.
"Van Poelgeest, A Exam Report", European Application No. 12793939.5; dated Oct. 7, 2019.
"Van Poelgeest, A Examination Report", EP Application No. 11 854 003.8-1113; dated Sep. 17, 2019.
"Vasat, Peter NonFinal OA", U.S. Appl. No. 12/785,064, filed May 21, 2010; Mailed Feb. 9, 2018.
"Vasat, Peter Notice of Allowance", U.S. Appl. No. 12/785,064, filed May 21, 2010; dated Sep. 12, 2016.

(56) References Cited

OTHER PUBLICATIONS

"Yuan, Minqiang Non-Final Office Action", Chinese Application No. 200920267201.2, dated Sep. 9, 2010.
"Yuan, Minquiang Non-Final Office Action", Chinese Application No. 200920267201.2, dated Jun. 4, 2010.
"Zeev, et al., "Family-centered Preparation for Surgery Improves Perioperative Outcomes in Children: A randomized Controlled Trial"", Anesthesiology, 106, pp. 65-74; https://anesthesiology.pubs.asahq.org/article.aspx?articleid=1922803 ; Jan. 2007.
"Summons to Attend Oral Proceedings", EP Application 11854003.8; Mailed Dec. 22, 2020.
"Summons to Attend Oral Proceedings", EP Application 12792423.1; Mailed Dec. 22, 2020.
"Summons to Attend Oral Proceedings", EP Application 12793939.5; Mailed Dec. 23, 2020.
Poon, Robert , "NonFinal Office Action", U.S. Appl. No. 16/258,231, filed Jan. 25, 2019; dated Mar. 31, 2021.

* cited by examiner

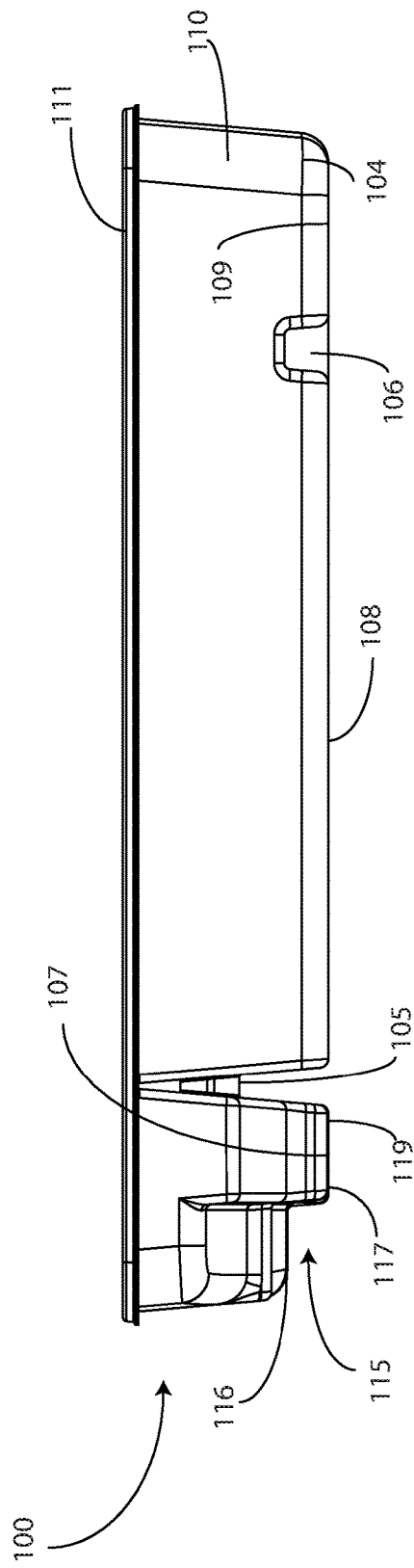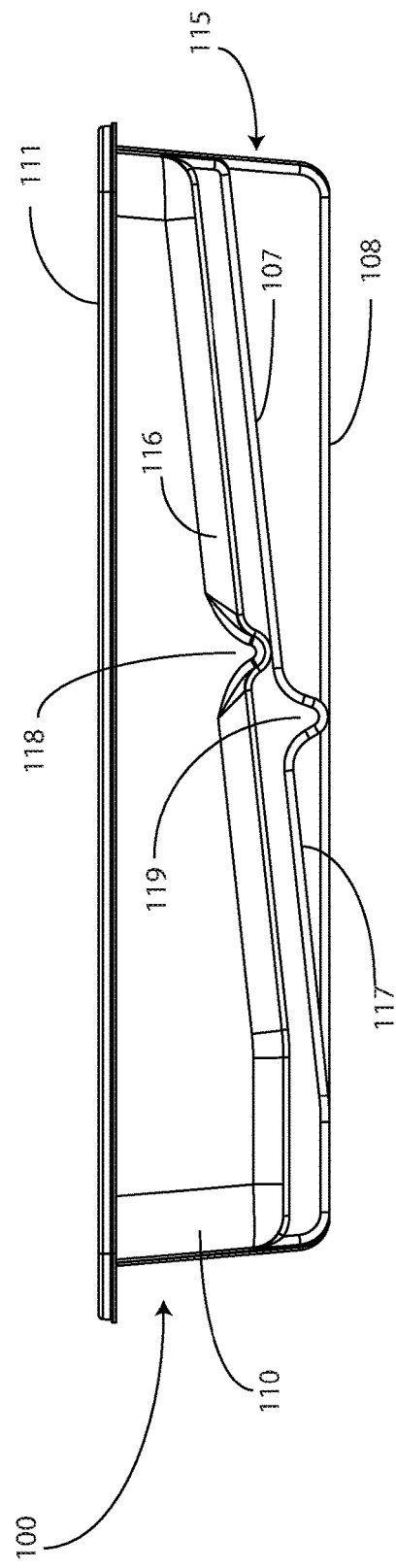

FOLEY CATHETER AND CORRESPONDING SINGLE-LAYER TRAY PACKAGING SYSTEM

BACKGROUND

Technical Field

This disclosure relates generally to Foley catheters, and more particularly to Foley catheter packaging systems.

Background Art

Medical devices, including surgical instruments, supplies, and so forth, are generally shipped from manufacturer to medical services provider in sterile packaging. For example, a scalpel may be shipped to a surgeon in a plastic, vacuum-sealed, sterile package. Similarly, bandages may be shipped in paper, plastic, or paper composite sterile wrappers. When the medical services provider is ready to use the medical supply, the sterile package is removed. The medical services provider then uses the object in accordance with the procedure being performed.

While conventional packaging works well for objects having a generally unchanging form factor, special considerations have to be taken into consideration for some medical supplies. By way of example, Foley catheters and their corresponding tubing and other flexible equipment is generally shipped in a coiled configuration. Once the sterile packaging is removed, the tubing and other coiled materials must be uncoiled prior to use. Care must be taken in shipping, unwrapping, and using coiled assemblies. For instance, if a Foley catheter is inadvertently bent, kinked, or otherwise damaged, it may no longer be suitable for use. It would be advantageous to have an improved packaging system for Foley catheters.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present disclosure.

FIG. 4 illustrates a front elevation view of one explanatory single-layer tray in accordance with embodiments of the disclosure.

FIG. 5 illustrates a cut-away, left elevation view of one explanatory single-layer tray in accordance with embodiments of the disclosure.

Figure 1:
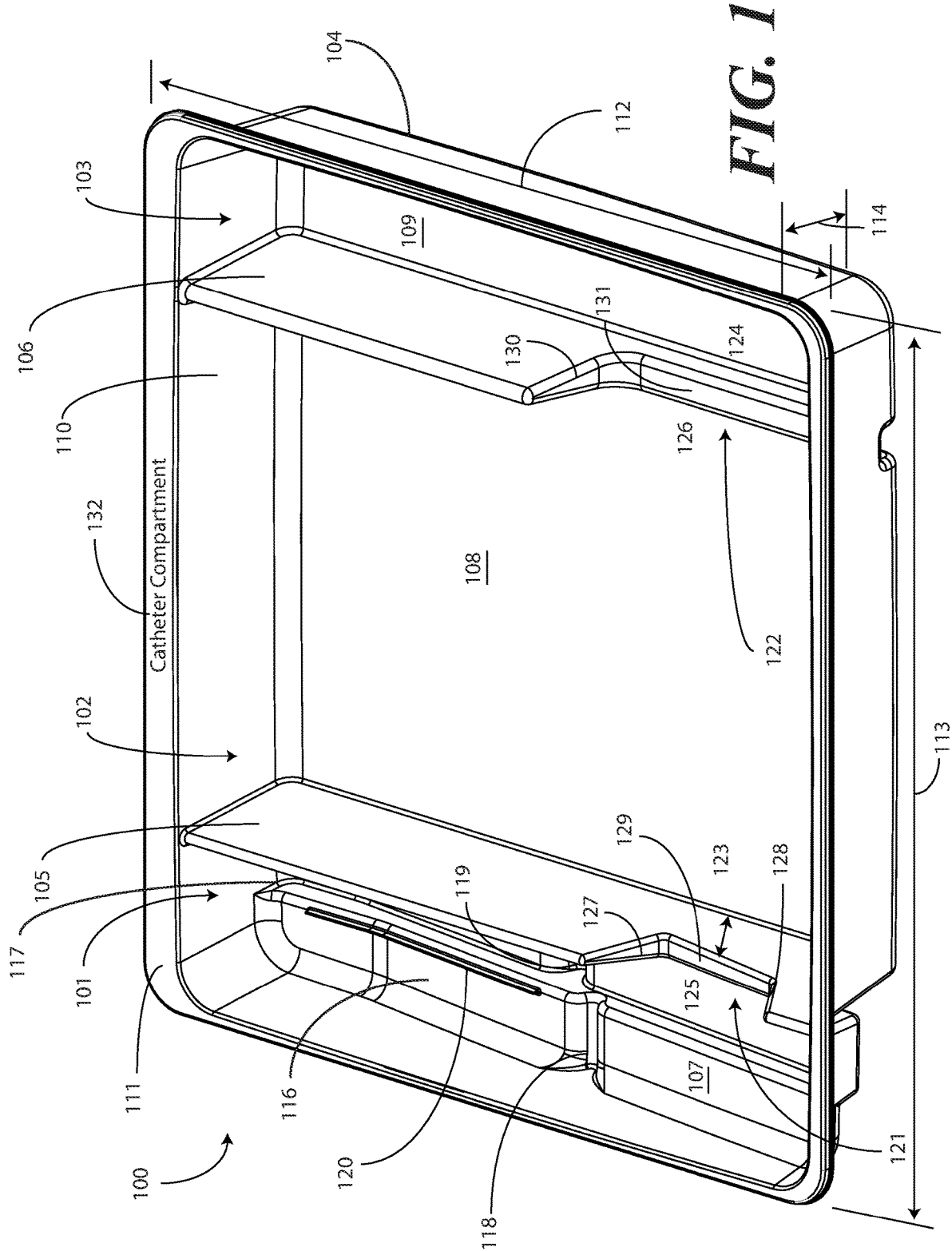
FIG. 1 illustrates a top, front, right perspective view of one explanatory single-layer tray in accordance with embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DISCLOSURE

Before describing in detail embodiments that are in accordance with the present disclosure, it should be observed that the embodiments reside primarily in combinations of method steps and apparatus components related to packaging Foley catheters, their corresponding coiled tubing, fluid drain bags, and other components in a single-layer tray. Alternate implementations are included, and it will be clear that any method steps may be executed out of order from that shown or discussed, including substantially concurrently or in reverse order, depending on the desired application. Accordingly, the apparatus components and method steps have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, it is expected that one of ordinary skill, notwithstanding possibly significant effort and many design choices motivated by, for example, available time, current technology, and economic considerations, when guided by the concepts and principles disclosed herein will be readily capable of generating such assemblies and executing such method steps with minimal experimentation.

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions.

As used herein, components may be "operatively coupled" when information can be sent between such components, even though there may be one or more intermediate or intervening components between, or along the connection path. The terms "substantially" and "about" are used to refer to dimensions, orientations, or alignments inclusive of manufacturing tolerances. Thus, a "substantially orthogonal" angle with a manufacturing tolerance of plus or minus two degrees would include all angles between 88 and 92, inclusive. Also, reference designators shown herein in parenthesis indicate components shown in a figure other than the one in discussion. For example, talking about a device (10) while discussing figure A would refer to an element, 10, shown in figure other than figure A.

Embodiments of the disclosure provide a medical procedure kit comprising a single-layer tray. In one or more embodiments, the single-layer tray comprises a first compartment and a second compartment. The first compartment is at least partially bounded by a first base member in one or more embodiments. The second compartment is at least partially bounded by a second base member in one or more embodiments.

In one or more embodiments, at least one syringe is situated within the first compartment. In one or more embodiments, a Foley catheter is situated in the second compartment. In one or more embodiments, the Foley catheter is operatively coupled to coiled tubing. In one or more embodiments, the coiled tubing is operatively coupled to a fluid drain bag. In one or more embodiments where the Foley catheter is disposed in the second compartment, the operatively coupled coiled tubing and fluid drain bag are also disposed within the second compartment.

In one or more embodiments, to provide additional protection for the Foley catheter and to further help ensure it remains sterile when the medical procedure kit is opened, the Foley catheter is placed at the bottom of the second compartment, with the operatively coupled coiled tubing and the operatively coupled fluid drain bag situated atop the Foley catheter. Said differently, in one or more embodiments, the Foley catheter and the coiled tubing are positioned between the second base member and the fluid drain bag. In one or more embodiments, the Foley catheter is positioned between the coiled tubing and the second base member.

Embodiments of the present disclosure further provide a medical procedure kit that includes medical products for performing a medical procedure. In one embodiment, the medical procedure kit is configured for a Foley catheterization procedure. Such an embodiment will be used herein for illustration purposes. However, it will be clear to those of ordinary skill in the art having the benefit of this disclosure that embodiments of the disclosure are not so limited. Other medical procedure kits for performing other procedures could be substituted for the illustrative Foley catheterization procedure kit disclosed herein by substituting other medical implements for the Foley catheterization implements.

When a Foley catheter assembly is inserted into a patient, sterile water may be used to inflate the balloon of the Foley catheter. Additionally, the Foley catheter may be coated in a lubricating jelly prior to insertion into the patient. Fluids and other samples may then be monitored and obtained from the patient as they pass into the Foley catheter, through the coiled tubing (which may be uncoiled at this point) and into a syringe via a Luer access port or into the fluid drain bag. Embodiments of the present disclosure provide a single-layer tray configured to accommodate not only the Foley catheter, the operatively coupled coiled tubing, and the operatively coupled fluid bag, but also syringes containing fluids such as sterile water or aqueous lubricants. Further, the single-layer tray can accommodate a sterile specimen jar for capturing samples taken from the patient as they pass into the Foley catheter, through the coiled tubing (which may be uncoiled at this point) and into a syringe via a Luer access port or into the fluid drain bag.

In addition to simply accommodating these corresponding medical devices, in one or more embodiments the single-layer tray is configured to provide the medical services provider with mnemonic devices instructing them in which order to use each device. For example, a compartment containing syringes, in one embodiment, includes a base member that presents each syringe at, for example, an easy to reach angle and/or at different heights based upon order in which each syringe is used in a Foley catheterization procedure.

Another advantage of embodiments of the present disclosure is that compartments have multi-purpose functionality. For example, in one embodiment, a compartment configured to accommodate a syringe having lubricating jelly disposed therein is also configured to be used as a lubricating jelly applicator or lubricating jelly application compartment. In one or more embodiments, a medical services provider first dispenses the lubricating jelly into the compartment from which the syringe was taken. The medical services provider then passes at least a tip of the Foley catheter from the second compartment into the first compartment and into the lubricating jelly. Advantageously, the tray not only serves as a shipping and storage container for an assembly of devices used with a Foley catheter procedure, but also as an application device to assist a medical services provider in using those products together, and without compromising the sterile field required for proper aseptic technique.

Figure 2:
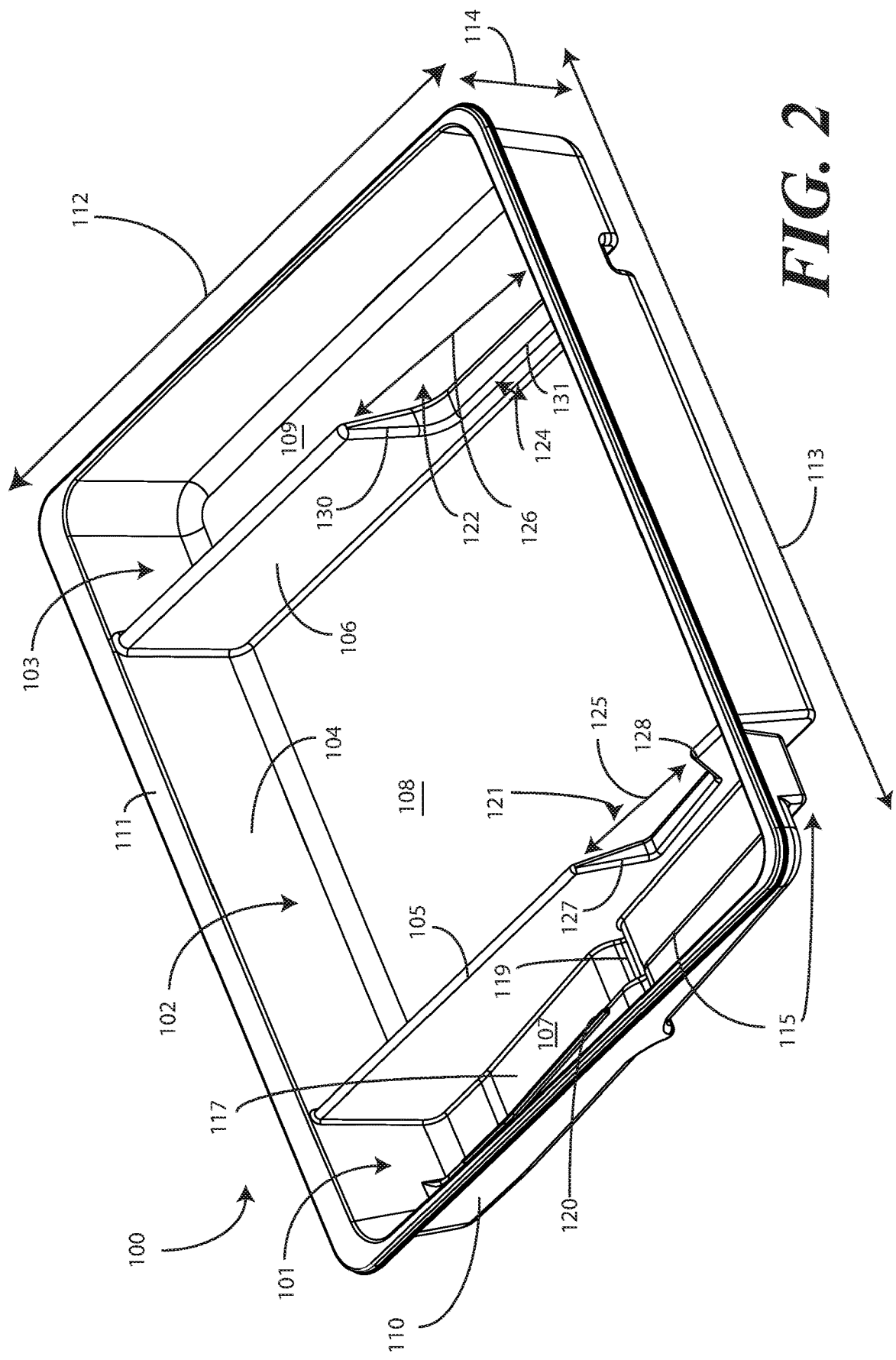
FIG. 2 illustrates a top, front, left perspective view of one explanatory single-layer tray in accordance with embodiments of the disclosure.
Figure 3:
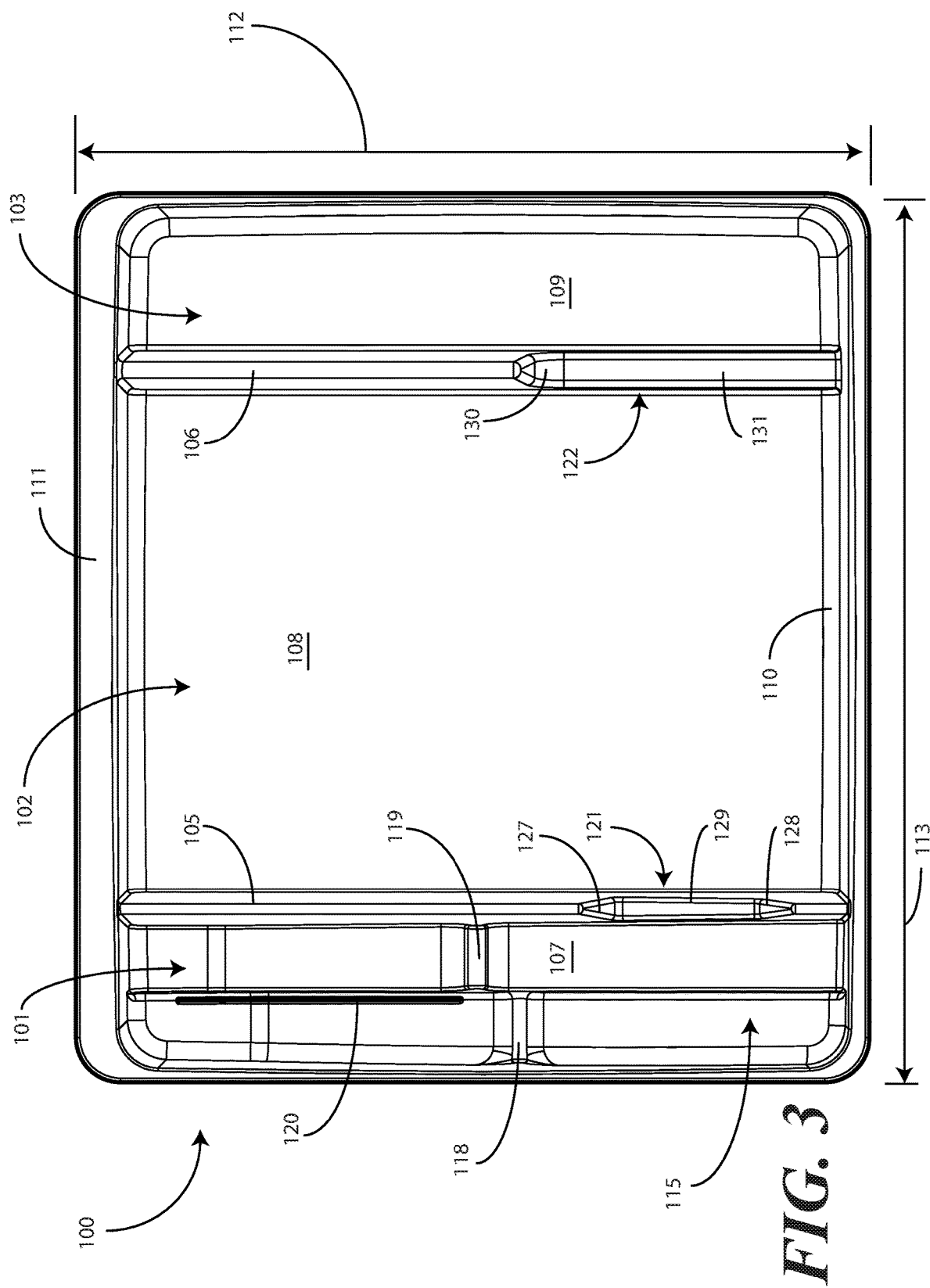
FIG. 3 illustrates a top plan view of explanatory single-layer tray in accordance with embodiments of the disclosure.
Figure 6:
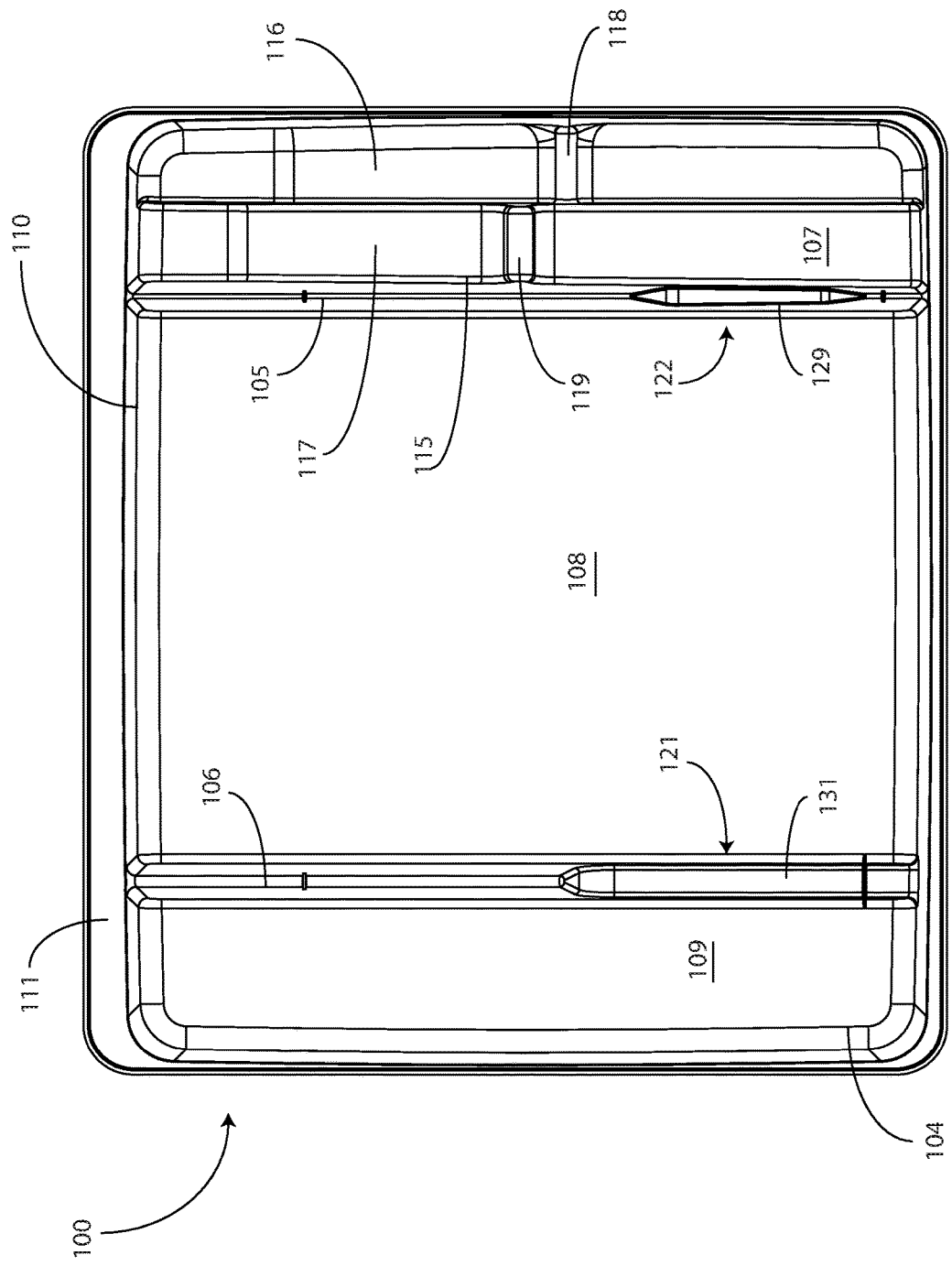
FIG. 6 illustrates a bottom plan view of one explanatory single-layer tray in accordance with embodiments of the disclosure.

Turning now to FIGS. 1-6, illustrated therein are views of one embodiment of a single-layer tray 100 configured to accommodate a Foley catheter, its operatively coupled coiled tubing, and its operatively coupled fluid drain bag in accordance with one or more embodiments of the disclosure. FIG. 1 illustrates a top, front right perspective view of the single-layer tray 100. FIG. 2 illustrates a top, front, left perspective view of the single-layer tray 100. FIG. 3 illustrates a top plan view of the single-layer tray 100. FIG. 4 illustrates a front elevation view of the single-layer tray 100. FIG. 5 illustrates a cut-away, left elevation view of one embodiment of a single-layer tray 100. Likewise, FIG. 6 illustrates a bottom plan view of the single-layer tray 100. For simplicity of discussion, these figures will be referred to collectively with like reference numerals referring to identical or functionally similar elements throughout the separate views.

The single-layer tray 100, in one embodiment, is formed by a contoured surface 104 that defines the various features and compartments of the single-layer tray 100. The contoured surface 104 of the single-layer tray 100 can be manufactured in various ways. For example, in one embodiment, the single-layer tray 100 can be thermally formed on a mold from a soft thermoplastic, such as styrene or polystyrene. In another embodiment, the single-layer tray 100 can be injection molded. In another embodiment, the tray can be poured on a mold using a quick setting plastic, epoxy, or resin. Other methods of manufacture will be obvious to those of ordinary skill in the art having the benefit of this disclosure.

Exemplary dimensions for one embodiment of the single-layer tray 100 are as follows: The length 112 can be between nine and twelve inches, such as ten inches. One illustrative length 112 may be 10.380 inches. Similarly, the width 113 can be between eight and eleven inches, such as nine inches.

One illustrative width 113 is 9.250 inches. The height 114 can be between one and three inches. One illustrative height 114 is 1.750 inches.

In one embodiment, the single-layer tray 100 includes three main compartments: a first compartment 101, a second compartment 102, and a third compartment 103. The first compartment 101 is separated from the second compartment 102 by a first barrier 105. The second compartment 102 is separated from the third compartment 103 by a second barrier 106.

In one embodiment, the compartments are open from the top of the single-layer tray 100—the top being opposite the base members of the single-layer tray 100—and are bounded on the bottom by a first base member 107, a second base member 108, and a third base member 109. The compartments are bounded on the sides by a perimeter wall 110. In the illustrative "open top" embodiment of FIG. 1, the perimeter wall 110 ends in a horizontal flange 111 extending substantially orthogonally from the perimeter wall 110. It will be clear to those of ordinary skill in the art having the benefit of this disclosure that embodiments other than that shown in FIG. 1 are possible without departing from the spirit and scope of the disclosure. For instance, the top of the single-layer tray 100 could have a hinged or snap-coupled lid that is opened or removed to reveal the compartments there beneath. Similarly, in one or more embodiments the horizontal flange 111 can be omitted, with each of the first compartment 101, the second compartment 102, and the third compartment 103 being bounded by a wall, be it the perimeter wall 110 or another wall, that extends distally from the various base members 107,108,109 to a terminating edge.

In one illustrative embodiment, the single-layer tray 100 is configured to hold or otherwise accommodate all of the necessary devices and materials to perform a Foley catheter-based procedure on a patient. Said differently, in one or more embodiments, the single-layer tray 100 is configured to hold not only the Foley catheter, its operatively coupled coiled tubing, and its operatively coupled fluid drain bag, but the medical devices corresponding to Foley catheter use as well. Using one illustrative procedure as an example, the following devices will be used: a syringe holding sterile water, a syringe holding lubricating jelly or another equivalent lubricant, a catheter assembly, skin cleansing or preparation materials, and a specimen jar. The various compartments and features of the single-layer tray 100 shown in FIGS. 1-6 will be described for use with these devices. As will be described in more detail below with reference to FIG. 9, additional objects can be included with the tray, such as one or more towels, a drape to cover the patient, rubber gloves, hand sanitizing materials, swab sticks, a securement device, a Foley insert tag, a printed instruction pamphlet, and so forth. The syringe holding sterile water, syringe holding lubricating jelly, the Foley catheter, its operatively coupled coiled tubing, and its operatively coupled fluid drain bag, and specimen jar are used for illustration purposes only, as it will be clear that other objects may be added to or substituted for these objects. Further, subsets of these objects may be used.

In one embodiment suitable for procedures using the syringe holding sterile water, syringe holding lubricating jelly, the Foley catheter, its operatively coupled coiled tubing, and its operatively coupled fluid drain bag, and specimen jar, the single-layer tray 100 is configured such that these objects are ordered in accordance with their order of use during the Foley catheterization procedure. For example, in one embodiment the single-layer tray 100 includes a first compartment 101 for accommodating one or more syringes, a second compartment 102 for accommodating the Foley catheter, its operatively coupled coiled tubing, and its operatively coupled fluid drain bag, and optionally one or more syringes, and a third compartment 103 for accommodating at least the specimen jar. These devices stowed in the various compartments will be illustrated and described with respect to FIG. 9 below. The discussion of FIGS. 1-6 will include the features of the single-layer tray 100 that make the single-layer tray 100 suitable for accommodating these devices.

For example, in one embodiment the first compartment base member 107 is contoured. Illustrating by example, the first compartment base member 107 can include features that hold any syringes stored within the first compartment 101 at different heights. In this illustrative embodiment, the first compartment base member 107 includes a stair-stepped contour 115 suitable that supports syringes at different heights.

Illustrating by example, a first step portion 116 of the stair-stepped contour 115 may be at a different height within the single-layer tray 100 than a second step portion 117 of the stair-stepped contour 115. In the illustrative embodiment of FIGS. 1-6, the first step portion 116—which is disposed farther from the first barrier 105 than the second step portion 117—is shallower than the second step portion 117. Said differently, the second step portion 117 is disposed at a greater depth within the single-layer tray 100 than the first step portion 116.

The contours of the first compartment 101 can serve as mnemonic device when for medical implements stored within the first compartment 101. For example, it may be intuitive that a higher syringe may need to be used first. Accordingly, placing this "first to be used" syringe on a higher step portion will indicate that this syringe should to be used first. This intuition is further enforced when the higher position is situated farther to the left in a left-to-right usage, i.e., like reading a book, configuration. Thus, a user receives a mnemonic reminder to use a syringe disposed on the first step portion 116 prior to a syringe disposed on the second step portion 117, as it is both higher and farther to the left.

Where syringes are stowed in the first compartment 101, the first compartment base member 107 can further be configured for syringe ease of use. For example, in one embodiment the first compartment base member 107 is inclined relative to other compartment base members. In the illustrative embodiment of FIGS. 1-6, the second compartment base member 108 and third compartment base member 109 are substantially coplanar with each other. Further, the second compartment base member 108 and third compartment base member 109 are generally flat in these views, although it will be clear to those of ordinary skill in the art having the benefit of this disclosure that contours could be incorporated into one or both of these base members. Illustrating by example, the first compartment base member 107 could be substantially flat.

In this illustrative embodiment, however, the first compartment base member 107 is configured to be inclined relative to one or both of the second compartment base member 108 and third compartment base member 109. As such, the stair-stepped contour 115 forms a ramp upon which syringes may be placed so that the plunger of each syringe is predisposed to project upward and out of the single-layer tray 100. Said differently, the stair-stepped contour 115 is configured such that the first step portion 116 and the second step portion 117 are disposed in a non-parallel orientation relative to the second compartment base member 108. This configuration makes it easier for a medical services provider to grasp the syringes and remove them from the single-layer tray 100.

The first compartment base member 107 may include other features suitable for accommodating one or more syringes as well. In one embodiment, any of the first compartment base member 107, the first step portion 116, or the second step portion 117 can include recesses 118,119 for accommodating a syringe flange. These recesses 118,119 generally function to prevent the syringes from sliding lengthwise within the first compartment 101. Similarly, in one embodiment any of the first compartment base member 107, the first compartment sidewalls, the first step portion 116, or the second step portion 117 include protrusions 120 that help to prevent the syringes from sliding laterally within the first compartment 101.

In one embodiment, one or both of the first barrier 105 and the second barrier 106 include optional openings disposed therein. In the illustrative embodiment shown in FIGS. 1-6, the first barrier 105 includes a first opening 121 between the first compartment 101 and the second compartment 102. Similarly, the second barrier 106 includes a second opening 122 between the second compartment 102 and the third compartment 103. Each of these openings has an opening depth associated therewith. Similarly, each opening has an opening width associated therewith. In the illustrative embodiment of FIGS. 1-6, the first opening 121 is bounded by a first opening base member 129 and two inclined first opening side members 127,128, while the second opening 122 is bounded by a second opening base member 131, an inclined second opening side member 130, and the perimeter wall 110.

While the opening depths can be the same, in one embodiment the opening depths are different. For example, in the illustrative embodiments of FIGS. 1-6, the first opening 121 has a first opening depth 123 that is less than the second opening depth 124 of the second opening 122. Similarly, in one embodiment the opening widths are different. For example, in the illustrative embodiments of FIGS. 1-6, the first opening 121 has a first opening width 125 that is less than the second opening width 126 of the second opening 122. Such a disparity in opening depths and widths, as well as the inclusion of inclined opening side members, provides an advantage in some applications.

For instance, in many Foley catheter procedures a pair of syringes—such as syringes having a one-half inch diameter—fits easily into the first compartment 101 when the single-layer tray 100 is made with the illustrative dimensions set forth above. However, some procedures require one or more of the syringes to be larger. Additionally, in still other procedures syringes are used in different orders. Where syringes that are larger in diameter are required, these larger syringes are capable of nesting within the first opening 121 and second opening 122. The inclined opening side members prevent the syringe from moving lengthwise, while the disparate opening heights present the plunger of the syringe to the medical services provider for easy removal from the single-layer tray 100. Where the syringes are used in different orders, or simply for design choice, one syringe can be placed in the first compartment 101, while another syringe can be placed in the second compartment 102, and so forth.

The stair-stepped contour 115, working in tandem with the first opening 121, gives the tray additional advantages over prior art catheter containers. For instance, the first compartment base member 107 allows the first compartment 101 to be used as a lubricant applicator for the catheter.

Specifically, the medical services provider may dispense the lubricating jelly into the first compartment 101 after removing the syringes therefrom. In one embodiment, this lubricating jelly is dispensed along the second step portion 117. Where included, and where lower than the first step portion 116, the second step portion 117 serves as a channel in which the lubricating jelly may spread. A medical services provider may then pass the at least a tip of the Foley catheter from the first compartment 101 into the second compartment 102, optionally through the first opening 121, and into the lubricating jelly. In one or more embodiments, the tip or more of the Foley catheter passes through the channel formed by the second step portion 117, i.e., along the second step portion 117 through the dispensed lubricating jelly. From there, the Foley catheter is passed out the top of the single-layer tray 100 to the patient.

This feature of the single-layer tray 100 greatly eases the application of lubricating jelly to the catheter when compared to prior art solutions. In one embodiment, the single-layer tray 100 is packaged with printed instructions showing the medical services provider how to apply lubricating jelly in this manner.

It will be clear to those of ordinary skill in the art having the benefit of this disclosure that alternative methods may be used to apply the lubricating jelly as well. For example, in another embodiment, the lubricating jelly is dispensed directly onto the Foley catheter and/or its operatively coupled tubing while these components are situated in or above either the first compartment 101 or the second compartment 102. Excess lubricant falling from the catheter tubing can then collect, and be retained, in any of the first compartment 101, the second step portion 117 of the first compartment 101, or the second compartment 102.

This particular feature highlights another advantage of the "compartmentalized" structure of various embodiments of the disclosure. As the single-layer tray 100 includes multiple compartments, various tasks associated with a Foley catheterization procedure can be completed while keeping the Foley catheter within the single-layer tray 100. The ability to keep the catheter in the single-layer tray 100 reduces the risk that the Foley catheter, its operatively coupled coiled tubing, and its operatively coupled fluid drain bag, or corresponding devices, will be contaminated with bacteria or microbes on other objects within the procedure room.

Illustrating by example, when the first compartment 101 is used to apply lubricating jelly to the Foley catheter or its operatively coupled coiled tubing, the lubricating jelly can be applied while these components are completely contained within the confines of the single-layer tray 100. Advantageously, this reduces the risk that the Foley catheter or its operatively coupled coiled tubing will become contaminated. This correspondingly reduces the risk of infection for the patient receiving the catheter.

Prior art systems, for example such as those in which the catheterization procedure components are shipped in separate and/or stacked containers, may contribute to substandard techniques in that the catheter can become contaminated when moving it from its shipping container. Consequently, the patient can be at an elevated risk of infection as the catheter is moved from one tray to another. Embodiments of the present disclosure solve this problem by providing a single-layer tray 100 with compartments. Further, in one embodiment the first compartment 101 allows the Foley catheter can stay in place during and after lubrication. By having easy access to the components disposed in the single-layer tray 100, the medical services provider can more easily prepare and use the components within the single-layer tray 100. This helps to minimize the risk of contaminating the patient or the sterile field during the procedure.

In one embodiment, the second step portion 117 is configured to be inclined at a shallower angle than the first step portion 116 in at least a portion opposite the recess 119 from the first opening 121. When configured in such a fashion, the second step portion 117 includes a "cutdown" so that the catheter can stay within the channel both during and after lubrication.

Additionally, the Foley catheter can be placed in both the first opening 121 and second opening 122 during lubrication. When positioned in this configuration, the second opening 122 helps to align the catheter with the first opening for easy passage through the lubrication channel formed by the second step portion 117.

The single-layer tray 100 of FIGS. 1-6 includes additional advantages over prior art catheter packaging as well. For example, in one embodiment, instructions 132 or other graphical indicia can be printed, placed upon, or molded into the tray. In this illustrative embodiment, the graphical indicia are molded into the horizontal flange 111. However, it can be molded into other portions of the single-layer tray 100, including the base members of the compartments, along the barriers, and so forth. In one embodiment, compartment designations can be placed above each compartment to ensure the medical services provider uses the correct device or material at the correct time. In another embodiment, expiratory dates for materials or devices disposed within the single-layer tray 100 may be molded into portions of the single-layer tray 100.

It will be obvious to those of ordinary skill in the art having the benefit of this disclosure that the disclosure is not so limited. Any number of various text or picture combinations can be printed on, placed upon, or molded into various parts of the tray. For instance, graphical indicia can be applied to the compartment base members in addition to the horizontal flange 111. Note that the horizontal flanges, in one embodiment, can terminate in downwardly protruding vertical flanges for increased stability during the printing process.

Another advantage of the single-layer tray 100 is that its compartmentalized configuration helps to reduce the risk of contaminating a patient or compromising the sterile nature of the components stored in the single-layer tray 100. Since Foley catheter, its operatively coupled coiled tubing, and its operatively coupled fluid drain bag, and medical devices corresponding to Foley catheter use, are stored within the same single-layer tray 100, the risk of cross-contamination between sterile work areas and non-sterile spaces is minimized. Further, by having the Foley catheter, its operatively coupled coiled tubing, and its operatively coupled fluid drain bag, and the devices corresponding to catheter use stowed in a one-level tray rather than a multi-level, stacked configuration, the medical services provider can more easily prepare and use the catheter and corresponding devices disposed within the single-layer tray 100.

Figure 7:
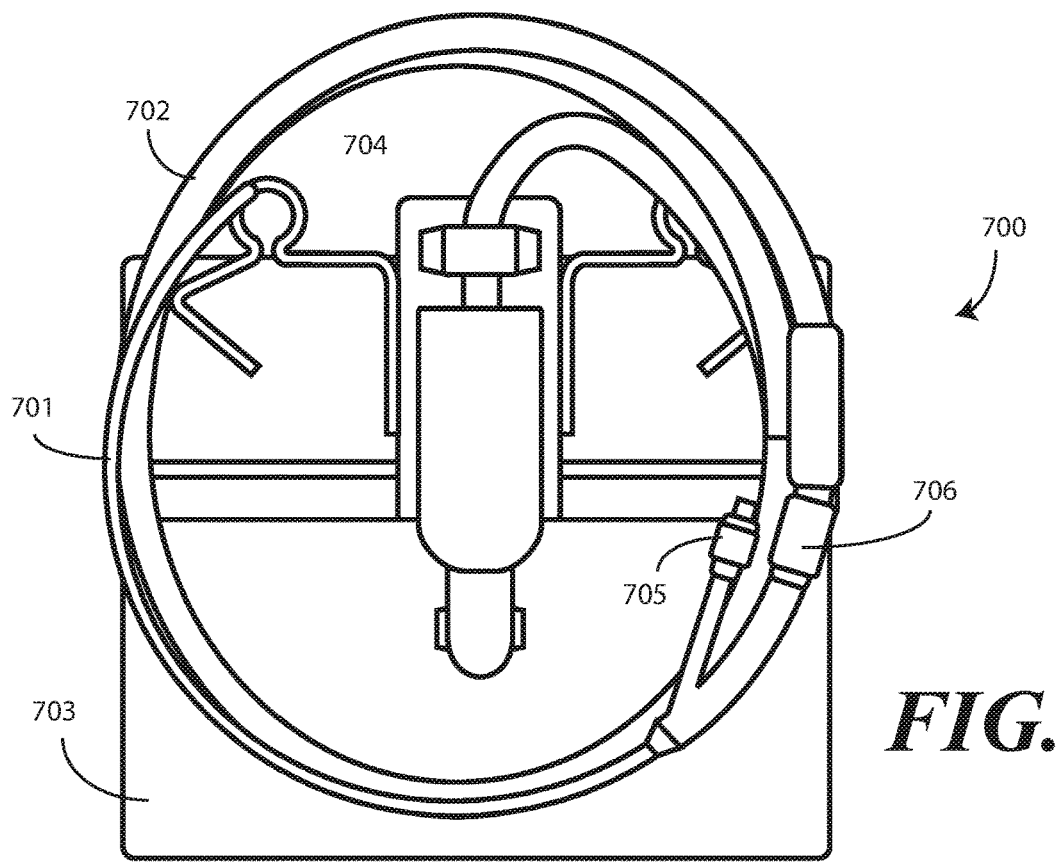
FIG. 7 illustrates a top plan view one explanatory Foley catheter, coiled tubing, and fluid drainage bag in accordance with one or more embodiments of the disclosure.

Turning now to FIG. 7, illustrated therein is one explanatory embodiment of a catheter assembly 700 configured in accordance with one or more embodiments of the disclosure. In one or more embodiments, the catheter assembly 700 comprises a Foley catheter 701, its operatively coupled coiled tubing 702, and its operatively coupled fluid drain bag 703. As shown in FIG. 7, the coiled tubing 702 is coupled between the Foley catheter 701 and the fluid drain bag 703.

A clip or other hanger 704 can be coupled to the fluid drain bag 703 so that the fluid drain bag 703 can be coupled to a stand, bedrail, or other object. In one or more embodiments the coiled tubing 702 may be coupled to the Foley catheter 701, and the fluid drain bag 703 coupled to the coiled tubing 702, before the assembly is placed in a tray. Alternatively the Foley catheter 701, the coiled tubing 702, and the fluid drain bag 703 can be separately stored in a tray, with each being coupled together once the tray is opened.

In one or more embodiments, the Foley catheter 701 includes an inflation port 705. A syringe containing sterile water or other fluid can be coupled to the inflation port 705. The sterile water or other fluid can be injected into the inflation port 705 so that the balloon of the Foley catheter 701 can be inflated. The Foley catheter 701 also includes a drainage port 706, which is operatively coupled to the coiled tubing 702.

The Foley catheter 701 is suitable for insertion into the urethra of a patient. In one or more embodiments, the Foley catheter 701 is an elongated, flexible device. The Foley catheter 701 can be manufactured from flexible material such as polymers, elastomers, flexible steel, or other materials. Other materials suitable for manufacturing the Foley catheter 701 will be obvious to those of ordinary skill in the art having the benefit of this disclosure.

In one or more embodiments, the Foley catheter 701 includes an insertion end and a second end, which is coupled to the coiled tubing 702 in one or more embodiments. A central lumen passes through the Foley catheter 701 so that fluids may pass from the insertion end to the second end, through the operatively coupled coiled tubing 702, and into the fluid drain bag 703.

When inserted into a patient, an inflatable retaining balloon (not shown) operatively coupled to the Foley catheter 701 can be inflated using the inflation port 705 to retain the Foley catheter 701 within the patient. In one or more embodiments, a balloon is inflated with sterile water to retain the insertion end of the Foley catheter 701 within the patient's bladder.

Figure 8:
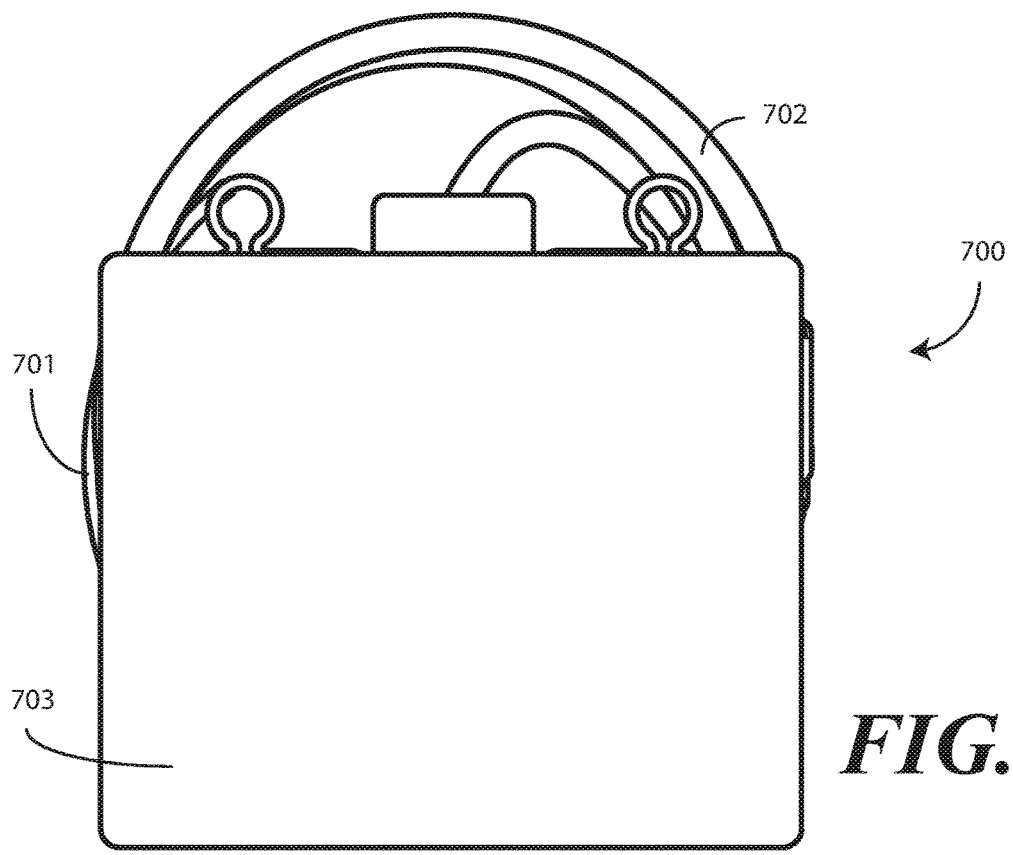
FIG. 8 illustrates a bottom plan view of one explanatory Foley catheter, coiled tubing, and fluid drainage bag in accordance with one or more embodiments of the disclosure.

Turning now to FIG. 8, illustrated therein is the catheter assembly 700 turned upside down. As shown, the coiled tubing 702 is disposed between the Foley catheter 701 and the fluid drain bag 703. Embodiments of the disclosure contemplate that inverting the catheter assembly 700 prior to placing the same in a tray offers numerous advantages. First, having the fluid drain bag 703 as the outer-most component provides an additional protective layer for both the coiled tubing 702 and the Foley catheter 701. This additional protective layer helps to ensure that the coiled tubing 702 and the Foley catheter 701 remain sterile, even after the packaging or tray is opened.

Second, inverting the catheter assembly 700 allows the fluid drain bag 703 to be removed from the tray or packaging first, and without disturbing the coiled tubing 702 and the Foley catheter 701. This provides more workspace within the tray or packaging for a medical services provider. Additionally, since the fluid drain bag 703 need not remain sterile, removing it from the tray or packaging will not risk contamination of the sterile field about the coiled tubing 702 and the Foley catheter 701.

Third, removal of the fluid drain bag 703 first allows it to be placed in a position that will help to increase the efficiency of fluid flow once the Foley catheter 701 is placed into a patient. Illustrating by example, when the fluid drain bag 703 is placed at a lower potential energy (with respect to gravity) than the patient, gravity will immediately assist in facilitating fluid flow through the coiled tubing 702 and the Foley catheter 701 once the Foley catheter 701 is inserted into a patient.

Figure 9:
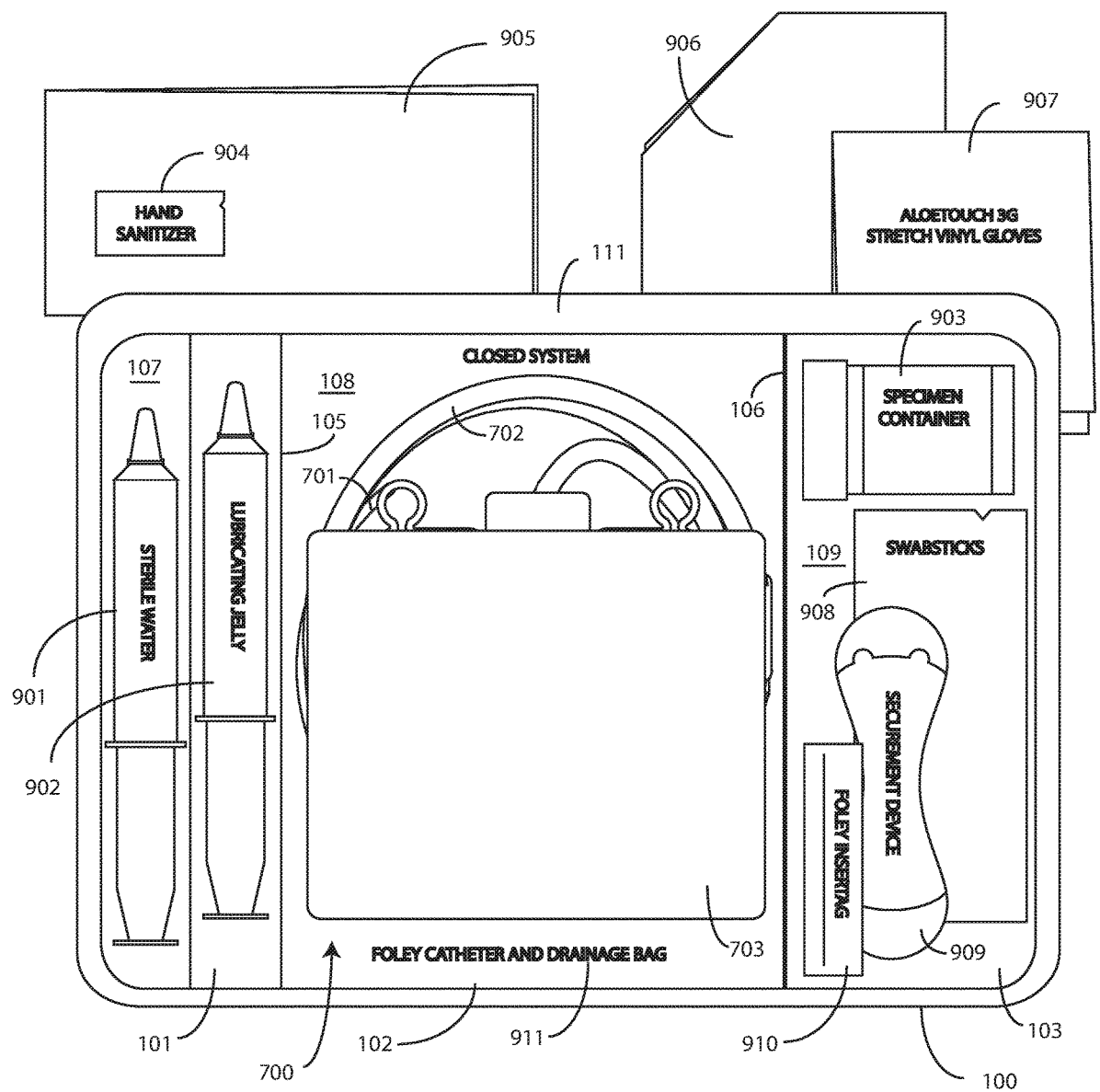
FIG. 9 illustrates a top plan view of one explanatory single-layer tray, with a Foley catheter and corresponding procedural devices disposed therein, in accordance with one or more embodiments of the disclosure.

Turning now to FIG. 9, illustrated therein is illustrated therein is a single-layer tray 100 having the catheter assembly 700 of FIG. 8, syringes 901,902, and a specimen container 903 stored therein as a catheter packaging system in accordance with one or more embodiments of the disclosure. The illustrative catheter packaging system of FIG. 9 includes a single-layer tray 100 having a first compartment 101, a second compartment 102, and a third compartment 103.

In this illustrative embodiment, the first compartment 101 is configured to accommodate syringes 901,902. The second compartment 102 is configured to accommodate a coiled medical device, such as catheter assembly 700. The third compartment 103 is configured to accommodate the specimen container 903. The third compartment 103 can accommodate other materials as well, including skin sanitizers 904 and cleansing liquids, solutions, or gels. Additional devices corresponding to Foley catheter use, including towels 905, drapes 906, rubber gloves 907, one or more swab sticks 908, a Foley catheter securement device 909, a Foley catheter insertion tag 910, and a Foley insertion tag, which is a dated and/or time stamped label that is secured to the catheter tubing once the Foley catheter 701 is inserted, and so forth, can be disposed in the single-layer tray 100 as well. As an illustration of this flexibility, one or more towels can be disposed beneath the catheter assembly in one or more embodiments.

In this illustrative embodiment, the catheter assembly 700 is inverted in the second compartment. This means that the Foley catheter 708 is adjacent to the second compartment base member 108, with the coiled tubing 702 atop the Foley catheter 701, and the fluid drain bag 703 atop the coiled tubing 702. Said differently, the Foley catheter 701 is positioned between the second compartment base member 108 and the coiled tubing. Similarly, the coiled tubing 702 is positioned between the Foley catheter 701 and the fluid drain bag 703. Alternatively, where towels or other components are placed beneath the catheter assembly 700, the Foley catheter 701 can be positioned between those components and the coiled tubing 702.

In this illustrative embodiment, the both the Foley catheter 701 and the coiled tubing 702 are positioned between the second base member 108 and the fluid drain bag 703. In this illustrative embodiment, the Foley catheter 701 is positioned between the coiled tubing 702 and the second base member 108.

As noted above, this inverted positioning of the catheter assembly 700 in the second compartment 102 offers numerous advantages over prior art designs. First, having the fluid drain bag 703 as the outer-most component provides an additional protective layer for both the coiled tubing 702 and the Foley catheter 701. This additional protective layer helps to ensure that the coiled tubing 702 and the Foley catheter 701 remain sterile, even after the single-layer tray 100, with its open top, is opened.

Second, inverting the catheter assembly 700 allows the fluid drain bag 703 to be removed from the second compartment 102 first, and without disturbing the coiled tubing 702 and the Foley catheter 701. This provides more workspace within the single-layer tray 100 for a medical services provider. Third, removal of the fluid drain bag 703 first from the single-layer tray 100 allows it to be placed in a position that will help to increase the efficiency of fluid flow once the Foley catheter 701 is placed into a patient.

As also noted above, in one embodiment the flange 111 or other parts of the single-layer tray 100, e.g., the first compartment base member 107, the second compartment base member 108, or the third compartment base member, can include instructions 911 or other graphical indicia. In one or more embodiments, the implements disposed in the various compartments 101,102,103 can have implements therein arranged in accordance with use during a Foley catheterization procedure. In one embodiment, the instructions 911 can be coordinated with this arrangement, indicating that components disposed in the first compartment 101 should be used first, components disposed in the second compartment 102 should be used next, and so forth. To assist the user in understanding workflow, arrows or other directional elements can be included on the flange 111 or other parts of the single-layer tray 100 as well.

As illustrated in FIGS. 1-6, each compartment of the single-layer tray 100 includes a compartment base member. Further, each compartment is separated by a barrier having an opening therein. A first barrier 105, optionally having a first opening therein, separates the first compartment 101 from the second compartment 102. Similarly, a second barrier 106, also optionally having a second opening 122 therein separates, the second compartment 102 from the third compartment 103.

Syringes 901,902 are disposed in the first compartment 101. In one or more embodiments, one syringe 902 contains a sterile liquid, such as sterile water. In one or more embodiments, another syringe 901 contains a lubricant, such as lubricating jelly. The lubricating jelly can be discharged into the first compartment 101 to lubricate at least a portion of the Foley catheter 701 in one or more embodiments when the Foley catheter 701 is passed from the second compartment 102 into the first compartment 101.

In one or more embodiments, one syringe 901 is supported at a different elevation within the single-layer tray 100 than the other syringe 902. The different elevations can be relative to each syringe 901,902, or to other components of the single-layer tray 100, such as the second compartment base member 108. Said differently, in one or more embodiments one syringe 901 is supported by the first compartment base member 107 at a shallower depth within the single-layer tray 100 than the depth of the second compartment base member 108. Further, where the first compartment base member 107 is inclined relative to other base members, in one or more embodiments one or both syringes 901,902 can be supported in a non-parallel configuration relative to the second compartment base member 108.

As noted above, some medical procedures will call for more materials than can be accommodated by a syringe capable of fitting within the first compartment 101. For such procedures, the single-layer tray 100 can be packed with larger syringes. A large syringe (not shown) can be supported laterally within the single-layer tray 100 when it is placed across the single-layer tray 100 such that it lies within one or more of the first compartment 101, the second compartment 102, or the third compartment 103. For example, the larger syringe can be placed within an opening of the first barrier 105 and an opening of the second barrier 106 (where included). Such a syringe can pass across the top of the catheter assembly 700. In other embodiments, the syringe (where fitting) can simply be placed adjacent to the catheter assembly 700 in the second compartment 102.

Once the necessary components are disposed within the single-layer tray 100, the tray can be sealed with a wrap to keep the internal components sterile. The wrap can be any of a number of types of material. In one embodiment, the wrap comprises a Central Sterile Reprocessing (CSR) wrap that is used widely by medical professionals in hospitals, ambulatory surgical centers, and the like during medical procedures. While a CSR wrap is one example of a wrap that can be used, it will be clear to those of ordinary skill in the art that other wraps, such as plastic, cotton, linen, paper, or combinations thereof, can be substituted without departing from the spirit and scope of the disclosure.

Using a CSR wrap as an illustrative example, in one embodiment the CSR wrap is folded about the single-layer tray 100 for sealing, and can be correspondingly unfolded to reveal the single-layer tray 100. Once unfolded, the CSR wrap can then be used in the catheter insertion process. For example, an unfolded CSR wrap can be used to provide a sterile field in which the single-layer tray 100 sits for unloading and subsequent use.

Printed instructions can then be attached to, disposed upon, or disposed within the single-layer tray 100. In one embodiment, the printed instructions include a health care services portion and a patient portion. The health care services portion can include instructions telling the health care services provider, for example, how to set up a sterile or otherwise clean work environment, how to prepare the catheter assembly 700 disposed within the tray, how to use the other devices within the tray, how to insert the catheter, how to secure the drainage bag to the catheter, how to empty the drainage bag, how to obtain a urine sample, and so forth. The instructions can include pictures or illustrations showing visually how the various steps should be done as well.

The patient portion can include helpful suggestions or instructions for the patient. The patient portion can be detachably coupled to the health care services portion, such as by a perforated line that is easily torn to separate the patient portion from the health care services portion. Examples of suggestions or instructions that may be included in the patient portion include information on what a catheter is, what the patient should understand about the catheter, how to reduce the chance of getting an infection, information about infections commonly associated with catheters, symptoms of infections commonly associated with catheters, and suggestions for home use of the catheter assembly 700. In one embodiment, the health care services portion may include an instruction for the health care services provider to detach the patient portion from the health care services portion and instructions to discuss the patient portion with the patient.

The health care services portion can tell the medical services provider how to perform a standard catheterization procedure. For instance, in one embodiment, the single-layer tray 100 is equipped with an adhesive label that can be used to identify the patient or specimen in the specimen container 903. Further, a label can be included to mark or otherwise identify the material in the fluid bag attached to the catheter. Such labels can include pre-printed fields, such as date, time and name. Further the printed instructions can notify the medical services provider that the devices disposed within the single-layer tray 100 are ordered corresponding to use during the catheterization procedure.

In another embodiment, the printed instructions can inform the medical services provider of special instructions. For instance, in one embodiment the printed instructions can inform the medical services provider not to leave a catheter in a patient for more than forty-eight hours without a physician's approval. Where the printed instructions include such information, the labels included in the single-layer tray 100 may have pre-printed fields for the time of insertion that can be filled in by the medical services provider performing the catheterization procedure.

Once the printed instructions have been affixed to, or placed with, within, or atop the single-layer tray 100, the assembly can be sealed in a sterile wrap such as a thermally sealed bag. The thermally sealed bag can optionally include a preformed opening. For example, in one embodiment, the opening can include one or more tabs that a health care services provider is instructed to pull to open the bag. Inclusion of a sterile wrap not only keeps the contents within the bag sterile, but also allows the instructions to be included with the tray assembly, yet outside the CSR wrap.

In one embodiment the printed instructions are disposed atop the CSR wrap such that the health care services portion of the printed instructions is disposed on the top of the printed instructions, with the patient portion being disposed adjacent to the CSR wrap, such as when the printed instructions are configured as an accordion-style folded instruction pamphlet. While the printed instructions of one embodiment are configured as a folded, printed, separate article disposed atop the CSR wrap, it will be clear to those of ordinary skill in the art having the benefit of this disclosure that the disclosure is not so limited. For example, in one embodiment the sterile wrap can be optional. In one embodiment, rather than including separate printed instructions, the instructions for use can be printed on the CSR wrap as well.

Additional instruction materials may be included with the completed assembly as well. For example, in one embodiment an adhesive instruction tag can be affixed to the sterile wrap. In another embodiment the instruction tag may be adhered to an outer packaging, that encloses the tray, the sterile wrap material or both. For example, in one embodiment the instruction tag can include information regarding whether a catheter procedure is needed. Text such as "Is there a valid clinical reason?" may be included under an instruction to "Stop" that includes the following information:

Before inserting the Foley catheter, at least one of the following conditions should exist:
Acute urinary retention or obstruction
Precise measurement of urinary output needed
Select surgical procedures
Open sacral or perineal wounds in incontinent patient
Prolonged immobilization
End of life care Further, checklist text may be included, such as "Checklist for Foley Catheter Insertion" included under the word "Check" that includes the following information:

Check Each Box Upon Completion:
Obtain order from physician/provider
Document clinical reason for insertion
Explain procedure to patient
Use smallest catheter possible
Perform hand hygiene
Follow aseptic technique Additional information may also be included, such as a fillable form that provides fields for the date and time of insertion of the catheter to be recorded, the name of the health care services provider, and the signature of the health care services provider. The above text for the instruction tag is illustrative only, and may be customized as desired by the manufacturer.

Figure 10:
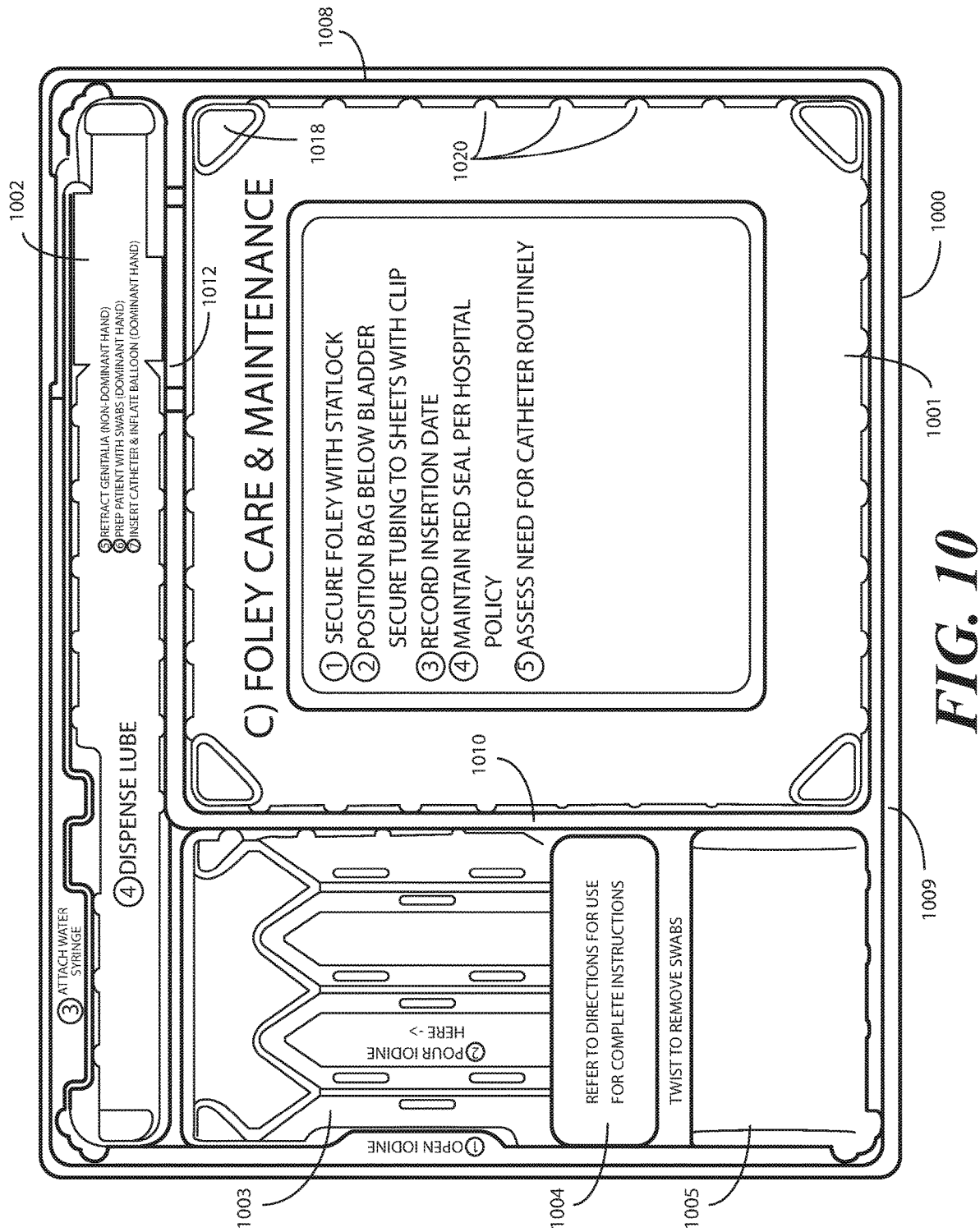
FIG. 10 illustrates a top plan view of another explanatory single-layer tray in accordance with one or more embodiments of the disclosure.

Turning now to FIG. 10, illustrated therein is another single-layer tray 1000 configured in accordance with one or more embodiments of the disclosure. In this illustrative embodiment, the single-layer tray 1000 comprises a main compartment 1001, a syringe or catheter compartment 1002, a swab compartment 1003, a small storage or overflow compartment 1004, and a corner storage compartment 1005. In one or more embodiments, the single-layer tray 1000 also includes one or more stiffening ribs 1020. Where included, the stiffening ribs 1020 can help to strengthen the single-layer tray 1000, as well as preventing bending.

In the illustrative catheter packaging system of FIG. 10, the syringe or catheter compartment 1002 defines a first section of the single-layer tray 1000. In the illustrative catheter packaging system of FIG. 10, the main compartment 1001 defines a second section of the single-layer tray 1000. In the illustrative catheter packaging system of FIG. 10, the swab compartment 1003, small storage or overflow compartment 1004, and corner storage compartment 1005 collectively define a third section of the single-layer tray 1000.

In one or more embodiments, the swab compartment 1003 includes a well and one or more channels configured to respectively hold the one or more swabs therein. In one or more embodiments, the overflow compartment 1004 fluidly connects to the well through the one or more channels.

In one or more embodiments, sides 1008 and 1009 of the single-layer tray 1000 define orthogonal inner walls. These orthogonal inner walls bound the main compartment 1001. They can further define a corner of the main compartment 1001 at an intersection location. The main compartment 1001 can include interior fillets 1018 at each corner. The fillets 1018, where included, can somehow provide a reinforcing function.

Interior partitions 1010 and 1012 can separate the main compartment 1001 from other compartments. In one or more embodiments, the two interior partitions 1010 and 1012 are shorter in height than are the sides 1008,1009. The one or more partitions 1010,1012 can separate, for example, the first section of the single-layer tray 1000, the second section of the single-layer tray 1000, the third section of the single-layer tray 1000, and so forth.

Figure 11:
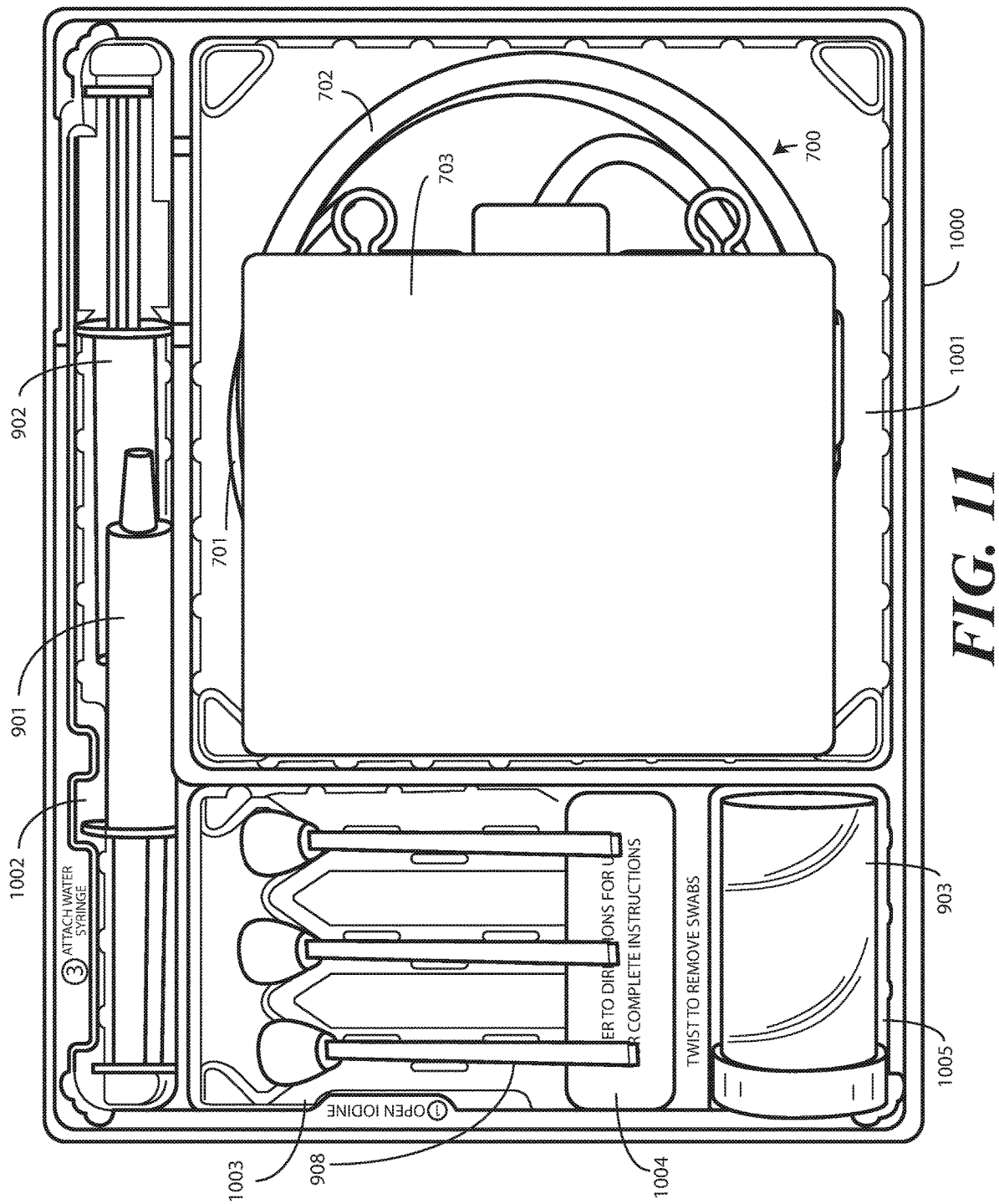
FIG. 11 illustrates a top plan view of another explanatory single-layer tray, with a Foley catheter and corresponding procedural devices disposed therein, in accordance with one or more embodiments of the disclosure.

Turning now to FIG. 11, illustrated therein is the single-layer tray 1000 from FIG. 10 having the catheter assembly 700 of FIG. 8, syringes 901,902, and a specimen container 903 stored therein as a catheter packaging system in accordance with one or more embodiments of the disclosure. In this illustrative embodiment, first section of the single-layer tray 1000 is configured to accommodate syringes 901,902. The second section of the single-layer tray 1000 is configured to accommodate a coiled medical device, such as catheter assembly 700. The third section of the single-layer tray 1000 is configured to accommodate the specimen container 903. The third section of the single-layer tray 1000 can accommodate other materials as well, such as one or more swab sticks 908.

In this illustrative embodiment, the catheter assembly 700 is inverted in the second section of the single-layer tray 1000. This means that the Foley catheter 708 is adjacent to the second compartment base member defining the base of the second section of the single-layer tray 1000, with the coiled tubing 702 atop the Foley catheter 701, and the fluid drain bag 703 atop the coiled tubing 702. Said differently, the Foley catheter 701 is positioned between the second compartment base member and the coiled tubing. Similarly, the coiled tubing 702 is positioned between the Foley catheter 701 and the fluid drain bag 703. Alternatively, where towels or other components are placed beneath the catheter assembly 700, the Foley catheter 701 can be positioned between those components and the coiled tubing 702.

In this illustrative embodiment, the both the Foley catheter 701 and the coiled tubing 702 are positioned between the second base member and the fluid drain bag 703. In this illustrative embodiment, the Foley catheter 701 is positioned between the coiled tubing 702 and the second base member.

As noted above, this inverted positioning of the catheter assembly 700 in the second compartment 102 offers numerous advantages over prior art designs. First, having the fluid drain bag 703 as the outer-most component provides an additional protective layer for both the coiled tubing 702 and the Foley catheter 701. This additional protective layer helps to ensure that the coiled tubing 702 and the Foley catheter 701 remain sterile, even after the single-layer tray 1000, with its open top, is opened.

Second, inverting the catheter assembly 700 allows the fluid drain bag 703 to be removed from the second compartment 102 first, and without disturbing the coiled tubing 702 and the Foley catheter 701. This provides more workspace within the single-layer tray 100 for a medical services provider. Third, removal of the fluid drain bag 703 first from the single-layer tray 1000 allows it to be placed in a position that will help to increase the efficiency of fluid flow once the Foley catheter 701 is placed into a patient.

Syringes 901,902 are disposed in the first section of the single-layer tray 1000. In one or more embodiments, one syringe 901 is supported at a different elevation within the single-layer tray 1000 than the other syringe 902. The different elevations can be relative to each syringe 901,902, or to other components of the single-layer tray 100, such as the second compartment base member. Said differently, in one or more embodiments one syringe 901 is supported in the first section of the single-layer tray 1000 at a shallower depth within the single-layer tray 1000 than second syringe 902.

Figure 12:
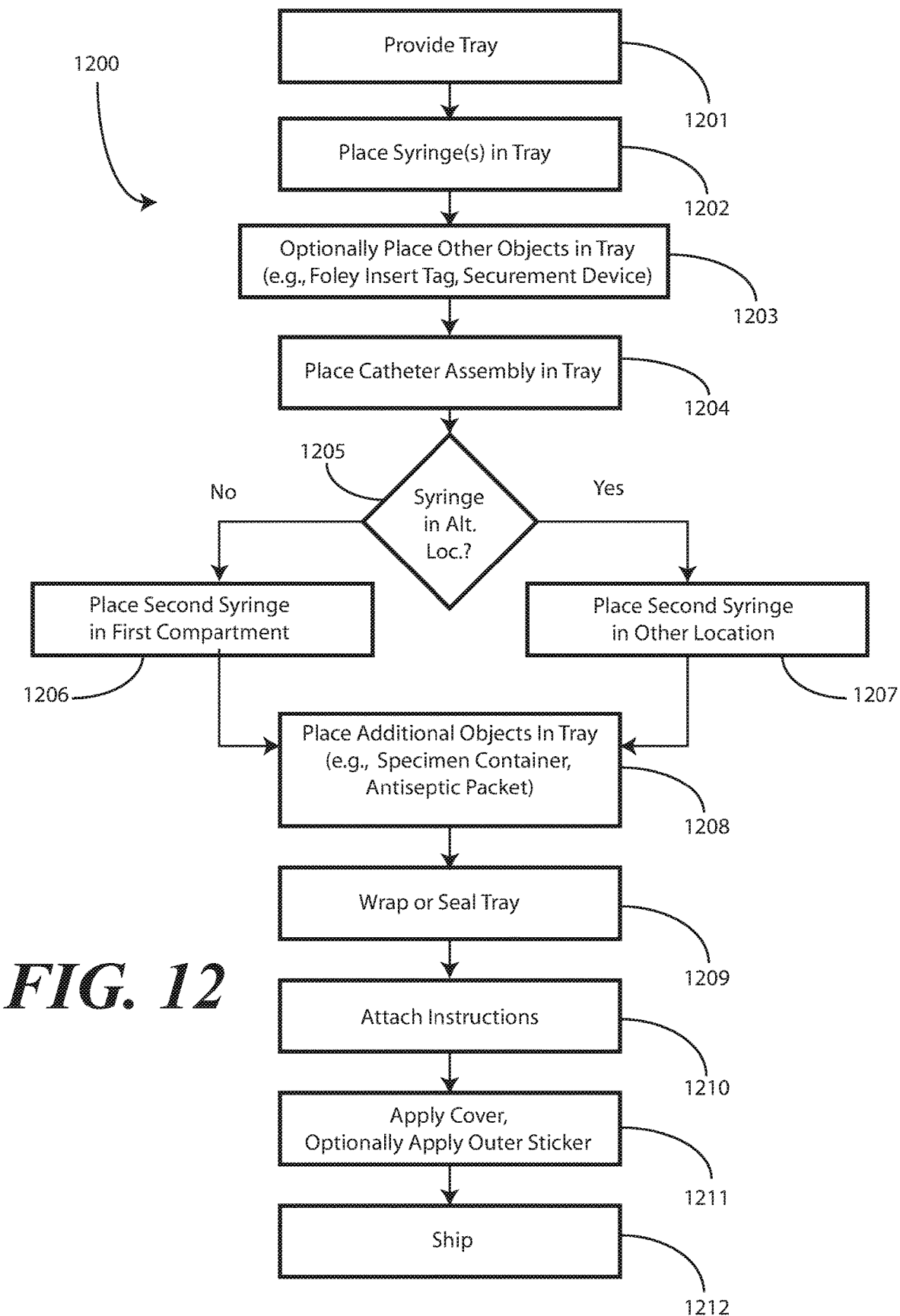
FIG. 12 illustrates one explanatory method in accordance with one or more embodiments of the disclosure.

Turning now to FIG. 12, illustrated therein is a method 1200 for manufacturing a packaged catheter assembly in accordance with embodiments of the disclosure. At step 1201, the manufacturer provides a single-layer tray having at least a first compartment for accommodating one or more syringes and a second compartment for accommodating a flexible medical device, such as a catheter assembly. As noted above, in one embodiment the first compartment will have a first compartment base member. The first compartment and second compartment can be separated by a first barrier, which can optionally have an opening therein.

Once the single-layer tray is procured, the manufacturer can dispose at least one syringe in the first compartment at step 1202. Optionally, at step 1203, the manufacturer may include additional components with the single-layer. For example, a catheter securement device, a Foley insert tag, or other complementary components may be included at this step 1203.

In one embodiment, as determined at decision 1205, a second syringe can be disposed in the first compartment at step 1206. In another embodiment, the second syringe will be disposed in the second compartment with the catheter assembly. In still another embodiment, the second syringe can be disposed laterally across one or more components.

At step 1204, the manufacturer will place the catheter assembly in the second compartment. In one or more embodiments, this step 1204 comprises inverting the catheter assembly prior to placement in the second compartment such that a coiled tubing of the catheter assembly, coupled between a Foley catheter and a fluid drain bag of the catheter assembly, is positioned or situated between the Foley catheter and the fluid drain bag. Accordingly, this results in the coiled tubing, the drain bag, and the Foley catheter being disposed within the compartment with the Foley catheter and the coiled tubing are positioned between the drain bag and the base member.

Other components may be disposed in the single-layer tray as well, including a specimen container that is disposed in a third compartment at step 1208. Further, other devices may be included, such as towels, drapes, printed instructions, one or more antiseptic packets, and so forth. These other devices can be disposed in various compartments within the single-layer tray.

At step 1209, the single-layer tray is sealed. This can be accomplished by folding a CSR wrap about the single-layer tray. In such an embodiment, the CSR wrap can be used during the catheter insertion procedure as well. At optional step 1210, the manufacturer can enclose printed instructions. In one embodiment, the printed instructions will direct a user to discharge contents of at least one syringe into the first compartment and to pass at least a portion of the catheter assembly through the opening and into the contents to lubricate the Foley catheter.

At step 1211, the manufacturer can place a sterile wrap about the tray and the printed instructions, where included. A sticker or other sealing device can be applied that indicates the contents to be sterile as well. At step 1212, the completed assembly can be shipped to a medical services provider.

Figure 13:
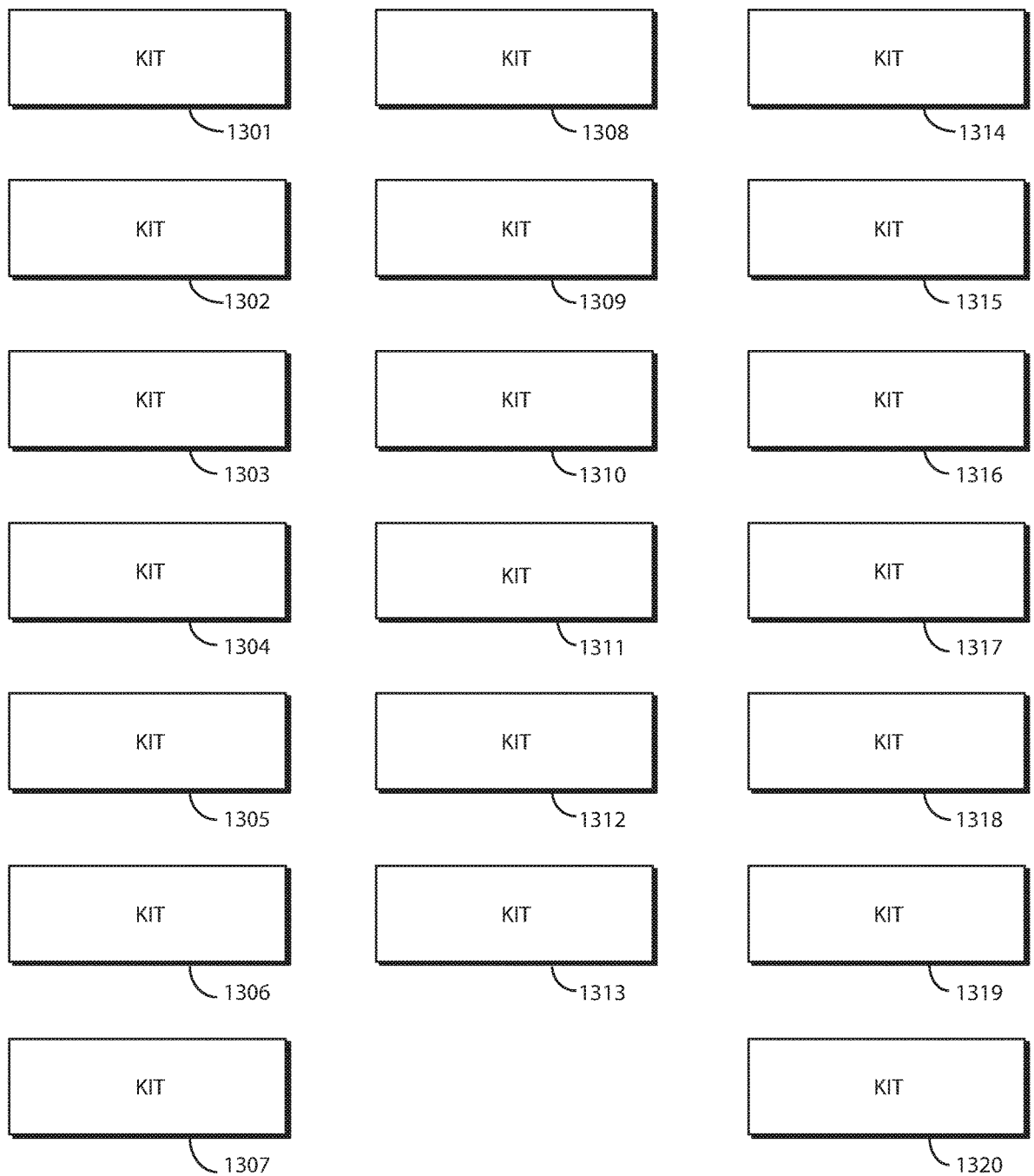
FIG. 13 illustrates various embodiments of the disclosure.

Turning now to FIG. 13, illustrated therein are various embodiments of the disclosure. At 1301, a medical procedure kit comprises a single-layer tray comprising a first compartment at least partially bounded by a first base member and a second compartment at least partially bounded by a second base member. At 1301, the medical procedure kit comprises at least one syringe situated within the first compartment. At 1301, the medical procedure kit comprises a Foley catheter, coupled to coiled tubing and a fluid drain bag, and disposed within the second compartment. At 1301, the Foley catheter and the coiled tubing are positioned between the second base member and the fluid drain bag.

At 1302, the Foley catheter of 1301 is positioned between the coiled tubing and the second base member. At 1303, the first compartment and second compartment of 1302 each define open top compartments.

At 1304, the single-layer tray of 1303 comprises a perimeter wall. At 1304, the first compartment is at least partially bounded by the perimeter wall. At 1305, the single-layer tray of 1303 comprises a perimeter wall. At 1305, the second compartment is at least partially bounded by the perimeter wall.

At 1306, the at least one syringe of 1303 comprises a first syringe and a second syringe. At 1307, the first compartment of 1306 defines a lubricating jelly application chamber to lubricate at least a portion of the Foley catheter.

At 1308, the single-layer tray of 1303 further comprises a third compartment bounded by a third base member. At 1309, the medical procedure kit of 1308 further comprises a specimen jar. At 1309, the specimen jar is positioned within the third compartment. At 1310, the medical procedure kit of 1308 further comprises one or more swab sticks positioned within the third compartment.

At 1311, a medical procedure kit comprises a single-layer tray. At 1311, the single-layer tray comprises a first section, a second section, and a third section. At 1311, each of the first section, the second section, and the third section is bounded by a base member. At 1311, one or more partitions separate at least one of the first section, the second section, or the third section from another one of the first section, the second section, or the third section.

At 1311, a Foley catheter, coupled to coiled tubing and a fluid drain bag, is disposed within the first section. At 1311, the Foley catheter and the coiled tubing are positioned between the base member of the first section and the fluid drain bag.

At 1312, the Foley catheter of 1311 is positioned between the coiled tubing and the base member of the first section. At 1313, the medical procedure kit of 1311 further comprises a syringe. At 1313, the syringe comprises a lubricant. At 1313, the syringe comprising lubricant is positioned in the second section.

At 1314, one or more swabs are positioned within the third section of the single-layer tray of 1313. At 1315, the medical procedure kit of 1314 further comprises a specimen jar. At 1315, the specimen jar is positioned within the third section.

At 1316, the third section of the single-layer tray 1315 comprises a swab compartment. At 1316, the swab compartment includes a well and one or more channels configured to respectively hold the one or more swabs therein. At 1316, the third section of the single-layer tray 1315 comprises an overflow compartment fluidly connected to the well through the one or more channels. At 1316, the third section of the single-layer tray 1315 comprises a corner storage compartment. At 1317, the specimen jar of 1316 is positioned within the corner storage compartment.

At 1318, a medical procedure kit comprises a single-layer tray comprising a compartment bounded at its bottom by a base member and a lubricating jelly application chamber. At 1318, a container of lubricating jelly disposed within the single-layer tray. At 1318, coiled tubing is coupled between a Foley catheter and a drain bag. At 1318, the coiled tubing, the drain bag, and the Foley catheter are disposed within the compartment with the Foley catheter and the coiled tubing positioned between the drain bag and the base member.

At 1319, the lubricating jelly application chamber of 1318 is configured to lubricate at least a portion of the Foley catheter with the lubricating jelly. At 1320, the Foley catheter of 1319 is positioned between the coiled tubing and the base member.

The following applications are incorporated herein by reference for all purposes: Ser. No. 14/793,455, filed Jul. 7, 2015; Ser. No. 13/860,902, filed Apr. 11, 2013; Ser. No. 13/155,026, filed Jun. 7, 2011; Ser. No. 61/352,140, filed Jun. 7, 2010; Ser. No. 61/352,155, filed Jun. 7, 2010; Ser. No. 61/428,944, filed Dec. 31, 2010; Ser. No. 61/437,796, filed Jan. 31, 2011; Ser. No. 12/495,148, filed Jun. 30, 2009; Ser. No. 12/647,515, filed Dec. 27, 2009; Ser. No. 13/153,265, filed Jun. 3, 2011; and Ser. No. 13/153,300, filed Jun. 3, 2011.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims. Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. A medical procedure kit, comprising:
a single-layer tray comprising a first compartment at least partially bounded by a first base member integral with the single-layer tray and a second compartment at least partially bounded by a second base member integral with the single-layer tray;
at least one syringe situated within the first compartment;
a Foley catheter, coupled to coiled tubing and a fluid drain bag, disposed within the second compartment;
wherein the Foley catheter and the coiled tubing are positioned between the second base member and the fluid drain bag, with the entirety of the fluid drain bag positioned atop at least a portion of the coiled tubing.

2. The medical procedure kit of claim 1, wherein the Foley catheter is positioned between the coiled tubing and the second base member.

3. The medical procedure kit of claim 2, wherein the first compartment and the second compartment each define open top compartments.

4. The medical procedure kit of claim 3, the single-layer tray comprising a perimeter wall, the first compartment at least partially bounded by the perimeter wall.

5. The medical procedure kit of claim 3, the single-layer tray comprising a perimeter wall, the second compartment at least partially bounded by the perimeter wall.

6. The medical procedure kit of claim 3, wherein the at least one syringe comprises a first syringe and a second syringe.

7. The medical procedure kit of claim 6, the first compartment defining a lubricating jelly application chamber to receive lubricant from one the at least one syringe for lubricating at least a portion of the Foley catheter.

8. The medical procedure kit of claim 1, wherein the Foley catheter and the coiled tubing are positioned between the second base member and the fluid drain bag such that the fluid drain can be removed from the single-layer tray without moving the Foley catheter.

9. The medical procedure kit of claim 8, further comprising a third compartment bounded by a third base member and a specimen jar positioned within the third compartment.

10. The medical procedure kit of claim 8, further comprising a third compartment bounded by a third base member and one or more swab sticks positioned within the third compartment.

11. A medical procedure kit, comprising:
a single-layer tray comprising a first section, a second section, and a third section, each bounded by a base member integral with the single-layer tray;
one or more partitions separating at least one of the first section, the second section, or the third section from another one of the first section, the second section, or the third section;
a Foley catheter, coupled to coiled tubing and a fluid drain bag, disposed within the first section;
wherein the Foley catheter and the coiled tubing are positioned between the base member of the first section and the fluid drain bag with the entirety of the fluid drain bag positioned atop at least some of the coiled tubing.

12. The medical procedure kit of claim 11, wherein the Foley catheter is positioned between the coiled tubing and the base member of the first section.

13. The medical procedure kit of claim 11, further comprising a syringe comprising lubricant, wherein the syringe comprising the lubricant is positioned in the second section.

14. The medical procedure kit of claim 13, further comprising one or more swabs positioned within the third section.

15. The medical procedure kit of claim 14, wherein the fluid drain bag can be removed from the single-layer tray without interfering with the Foley catheter.

16. The medical procedure kit of claim 15, wherein the third section comprises:
a swab compartment including a well and one or more channels configured to respectively hold the one or more swabs therein;
an overflow compartment fluidly connected to the well through the one or more channels; and
a corner storage compartment.

17. The medical procedure kit of claim 16, further comprising a specimen jar positioned within the third section, wherein the specimen jar is positioned within the corner storage compartment.

18. A medical procedure kit, comprising:
a single-layer tray comprising a compartment bounded at its bottom by a base member that is integral with the single-layer tray and a lubricating jelly application chamber;
a container of lubricating jelly disposed within the single-layer tray; and
a coiled tubing coupled between a Foley catheter and a drain bag, wherein the coiled tubing, the drain bag, and the Foley catheter are disposed within the compartment with at least a portion the Foley catheter and at least some of the coiled tubing positioned between an entirety of the drain bag and the base member.

19. The medical procedure kit of claim 18, wherein the lubricating jelly application chamber is configured to lubricate at least a portion of the Foley catheter with the lubricating jelly.

20. The medical procedure kit of claim 18, wherein the Foley catheter is positioned between the coiled tubing and the base member.

* * * * *